(12) United States Patent
Park et al.

(10) Patent No.: US 8,431,543 B2
(45) Date of Patent: Apr. 30, 2013

(54) CHITOSAN BASED POLYMER CONJUGATE AND A METHOD FOR PRODUCING THE SAME

(75) Inventors: Myung-Ok Park, Seoul (KR); Yu-Kyoung Oh, Seoul (KR); Sang Myoung Noh, Seoul (KR); Sung Sik Bang, Gyeonggi-do (KR); Myung Suk Kim, Seoul (KR)

(73) Assignee: Engene, Inc, Vancouver, B.C. (CA)

( * ) Notice: Subject to any disclaimer, the term of this patent is extended or adjusted under 35 U.S.C. 154(b) by 456 days.

(21) Appl. No.: 12/522,215

(22) PCT Filed: Jan. 7, 2008

(86) PCT No.: PCT/KR2008/000079
§ 371 (c)(1),
(2), (4) Date: Jan. 12, 2010

(87) PCT Pub. No.: WO2008/082282
PCT Pub. Date: Jul. 10, 2008

(65) Prior Publication Data
US 2010/0113559 A1    May 6, 2010

(30) Foreign Application Priority Data

Jan. 5, 2007  (KR) .................. 10-2007-0001715

(51) Int. Cl.
*A61K 48/00*   (2006.01)
*A61P 43/00*   (2006.01)
*C12Q 1/68*    (2006.01)

(52) U.S. Cl.
USPC .................. 514/44 A; 514/44 R; 530/345

(58) Field of Classification Search .......... None
See application file for complete search history.

(56) References Cited

U.S. PATENT DOCUMENTS

| 5,858,784 | A | 1/1999 | Debs et al. |
| 6,020,457 | A | 2/2000 | Klimash et al. |
| 6,596,699 | B2 | 7/2003 | Zamora et al. |
| 6,602,952 | B1 | 8/2003 | Bentley et al. |
| 6,730,742 | B1 | 5/2004 | Demain |
| 6,958,325 | B2 * | 10/2005 | Domb .................. 514/54 |
| 2004/0071654 | A1 | 4/2004 | Anderson et al. |
| 2004/0156904 | A1 | 8/2004 | Saltman et al. |
| 2006/0008910 | A1 | 1/2006 | MacLachlan et al. |
| 2006/0093674 | A1 | 5/2006 | Slobodkin et al. |
| 2008/0085242 | A1 * | 4/2008 | Artursson et al. .......... 424/9.1 |
| 2009/0110719 | A1 * | 4/2009 | Roy et al. .................. 424/450 |

FOREIGN PATENT DOCUMENTS

| KR | 10-2001-0101002 | 11/2001 |
| KR | 10-2002-0085981 | 11/2002 |
| WO | 00/27886 | 5/2000 |

OTHER PUBLICATIONS

Hongtao LV et al., "Toxicity of cationic lipids and cationic polymers in gene delivery," Journal of Controlled Release 114, 2006, pp. 100-109.
Y-K Oh et al.; Prolonged organ retention and safety of plasmid DNA administered in polyethylenimine complexes; Gene Therapy, vol. 8, 2001; pp. 1587-1592.
International Search Report of PCT/KR2008/000079; mailing date Mar. 11, 2008; pp. 3.
W.G Liu et al., "A chitosan-arginine conjugate as a novel anticoagulation biomaterial," Journal of Materials Science: Materials in Medicine 15 (2004), pp. 1199-1203.
Hai-Quan Mao et al, "Chitosan-DNA nanoparticles as gene carriers: synthesis, characterization and transfection efficiency," Journal of Controlled Release 70 (2001), pp. 399-421.
D. Zhu et al., "Enhancement of transfection efficiency for HeLa cells via incorporating arginine moiety into chitosan," Chinese Science Bulletin, Dec. 2007, vol. 52, No. 23, pp. 3207-3215.

* cited by examiner

*Primary Examiner* — Sean McGarry
(74) *Attorney, Agent, or Firm* — Todd Lorenz; Arnold + Porter LLP

(57) ABSTRACT

The present invention relates to a conjugate of chitosan and polyamine polymer that is useful for transferring a desired gene medicine into cells, and a method for preparing the same. In particular, the present invention relates to a double conjugate that is prepared by 1 in king poly-L-arginine to low molecular weight chitosan or triple conjugate that is prepared by additionally linking polyethylene glycol (PEG) to the double conjugate, and a method for preparing the same. The chitosan based cationic polymer conjugate of the present invention forms a complex with negatively charged gene medicine such as plasmid DNA and small interfering RNA to efficiently transfer the desired gene medicine into cells with low cytotoxicity. Accordingly, the conjugate can be used as an effective delivery system for in vivo administration of gene medicine.

20 Claims, 13 Drawing Sheets

M: 1 kb plus ladder (size marker)
1: Group treated with siRNA only
2: Group treated with complex of 0.01 ug of polymer and siRNA
3: Group treated with complex of 0.1 ug of polymer and siRNA
4: Group treated with complex of 1 ug of polymer and siRNA
5: Group treated with complex of 10 ug of polymer and siRNA Un: Untreated group Nak: Group treated with siRNA only Lipo: control group (treated with lipofectamine/siRNA complex)

1: Untreated group
2: Control group (lipofectamine/siRNA complex)
3: Example 14-1/siRNA complex
4: Example 18-1/siRNA complex
5: Example 1-2/siRNA complex
6: Example 9-3/siRNA complex

CHITOSAN BASED POLYMER CONJUGATE AND A METHOD FOR PRODUCING THE SAME

TECHNICAL FIELD

The present invention relates to a chitosan conjugate that is useful for in vivo administration and delivery of gene medicines such as small interfering RNA and plasmid DNA, and a method for preparing the same. In particular, the present invention relates to double conjugates that are prepared by linking poly-L-arginine to chitosans having different molecular weights as a template or triple conjugates that are prepared by additionally linking polyethylene glycol (PEG) to the double conjugates, and a method for preparing the same.

BACKGROUND ART

In general, gene medicines are negatively charged due to their structural characteristic, and thus many studies have been conducted on in vivo delivery system, which is a complex prepared by associating negative charge of small interfering RNA or plasmid DNA with positive charge of cationic polymers such as polyethyleneimine and polylysine, or cationic phospholipid nanoparticles.

Cationic phospholipid nanoparticles are disclosed in U.S. Pat. No. 5,858,784 and US Patent Publication NO. 20060008910A1, in which cationic lipids are mixed with phospholipids in a predetermined ratio to prepare particles such as cationic liposome, the particles are mixed with nucleic acid to prepare a complex of cationic phospholipids particles and nucleic acid, and then the complex is introduced into a cell line to improve gene expression. Cationic polymers have been also studied as a gene delivery vehicle, which are disclosed as follows: DEAE dextran, polylysine having repeating lysine units, and polyethyleneimine having repeating ethyleneimine units in U.S. Pat. No. 6,020,457, polyamino-ester in US Patent Publication NO. 20040071654A1, and a biodegradable cationic copolymer in US patent Publication NO. 20060093674A1.

As a gene delivery vehicle, the synthetic polymers are advantageous in that they are easily prepared, not limited by the size of gene to be introduced, generate fewer side effects that may be induced by immunogenic viral surface protein upon repeated administration, cause no safety problems due to viral genes, and require lower production cost in a commercial process, as compared to viral vectors including lentiviral, adenoviral and retroviral vectors. However, there are drawbacks in that the delivery systems using such cationic polymers have lower transfection efficiency as compared to viral vectors that are effectively transferred via cell surface receptors, and induce cytotoxicity (*J. Control. Release* (2006) 114, 100-109). Another drawback of the cationic polymer mediated gene transfer is that it does not greatly prolong the half life in blood (*Gene Ther.* (2001) 8, 1857-1592).

Among cationic polymers, chitosan has been studied as a promising candidate for gene delivery because it has several advantages such as industrial availability and biocompatibility. However, it has to overcome such problems as solubility and low transfection efficiency. In order to improve such problems, U.S. Pat. No. 6,730,742 (2004) discloses that chitosan is conjugated to polyethylene glycol to prepare a polymer conjugate, and the polymer conjugate is used as a gene delivery system for mucosal administration. However, there is a limitation in that only the addition of polyethylene glycol does not significantly improve the gene transfer efficiency.

Accordingly, the present inventors have made an effort to improve gene transfer efficiency and stability in blood by using chitosan. They found that a double conjugate that is prepared by linking a cationic polyamine to chitosan or a triple conjugate that is prepared by additionally linking a biocompatible polyethylene glycol (PEG) to the double conjugate is used to reduce cytotoxicity and improve gene transfer efficiency or retention time in blood, thereby completing the present invention.

DISCLOSURE

Technical Problem

It is an object of the present invention to provide a chitosan based cationic polymer conjugate prepared by covalently linking polyamine to chitosan or a chitosan based cationic polymer conjugate prepared by additionally linking polyethylene glycol to the chitosan based polymer conjugate, in which the conjugates reduce cytotoxicity and improve the in vivo transfer efficiency of desired gene medicines such as small interfering RNA or plasmid DNA.

It is another object of the present invention to provide a gene delivery composition for transferring gene medicines in vivo, comprising the chitosan based cationic polymer conjugate.

It is still another object of the present invention to provide a method for preparing the chitosan based cationic polymer conjugate.

It is still another object of the present invention to provide a gene delivery composition for increasing the retention time of gene medicine in blood, comprising the chitosan based cationic polymer conjugate.

BEST MODE

Figure 1:
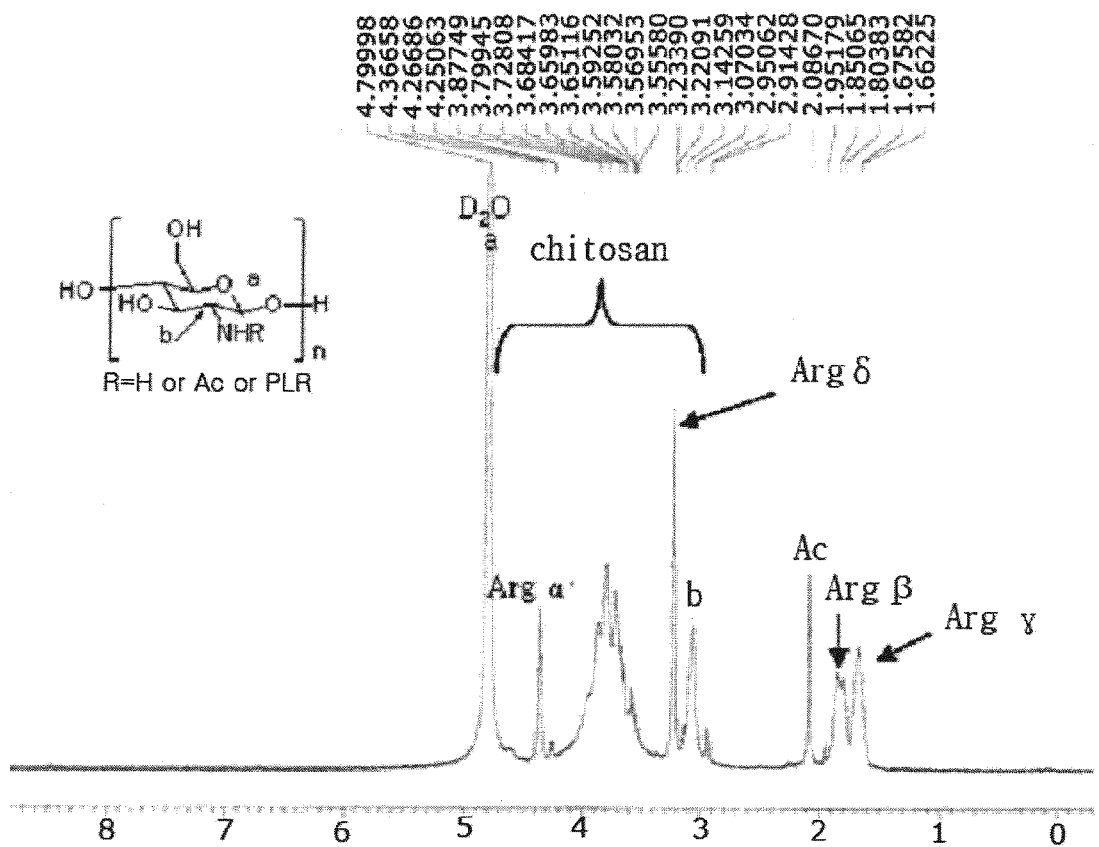
FIG. 1 shows the result of $^1$H NMR of chitosan-poly-L-arginine conjugate.
Figure 2:
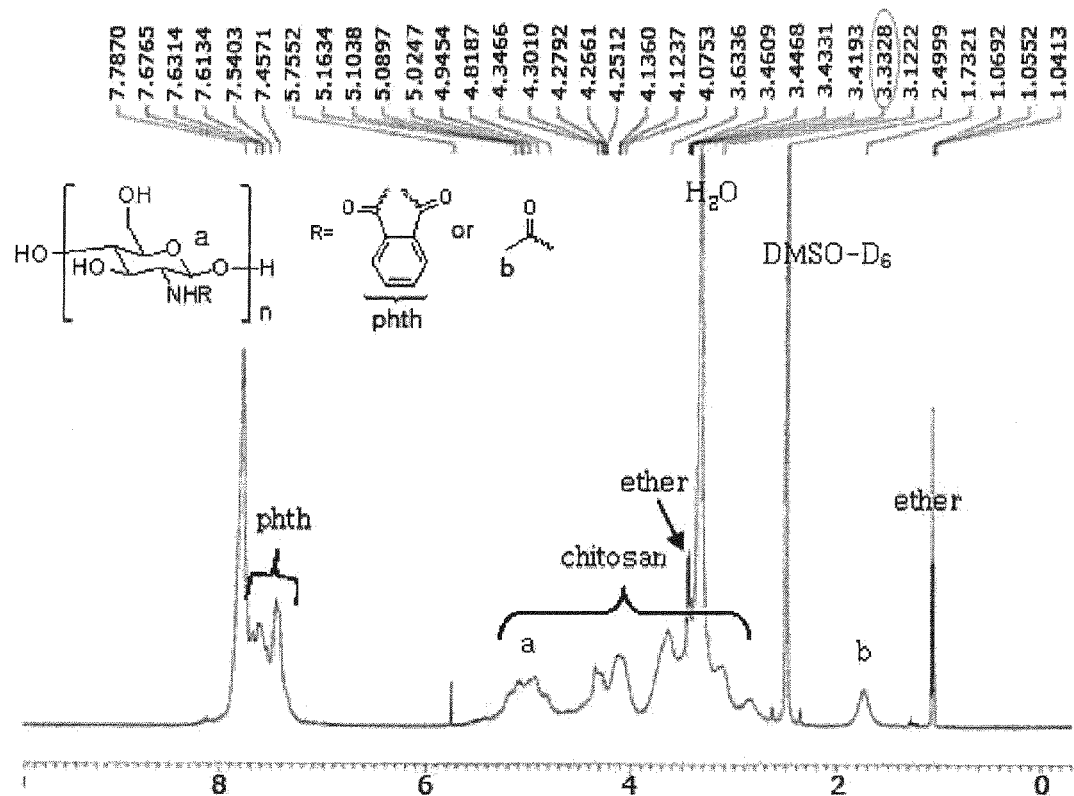
FIG. 2 shows the result of $^1$H NMR of phthaloyl chitosan, of which a reactive group is protected with phthalic acid.
Figure 3:
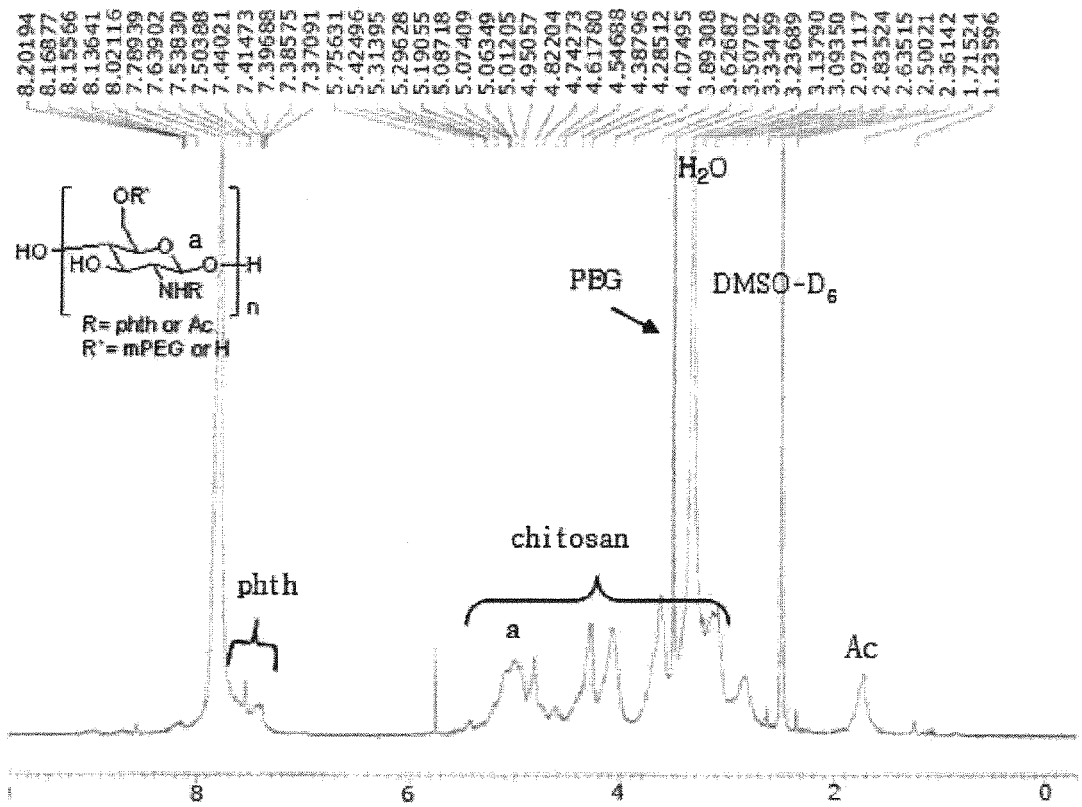
FIG. 3 shows the result of $^1$H NMR of 5'-mPEG2K-phthaloyl-chitosan conjugate.
Figure 4:
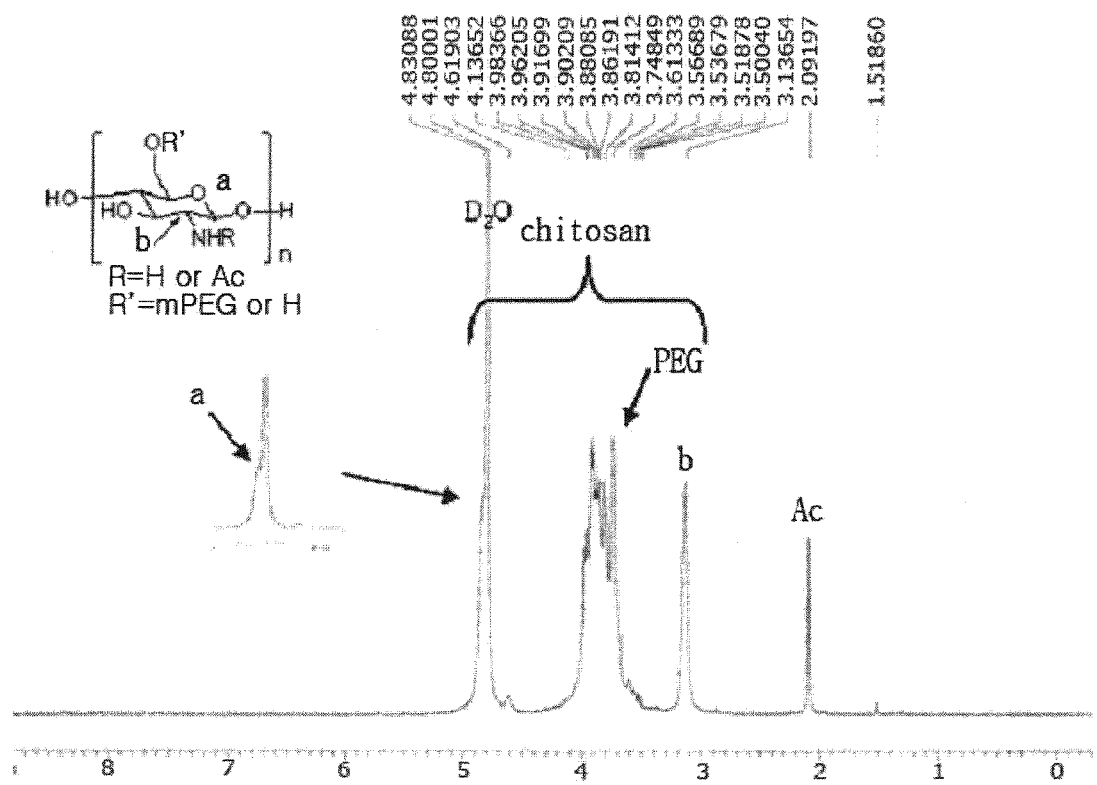
FIG. 4 shows the result of $^1$H NMR of 5'-mPEG2K-chitosan conjugate after deprotection of phthalic acid.
Figure 5:
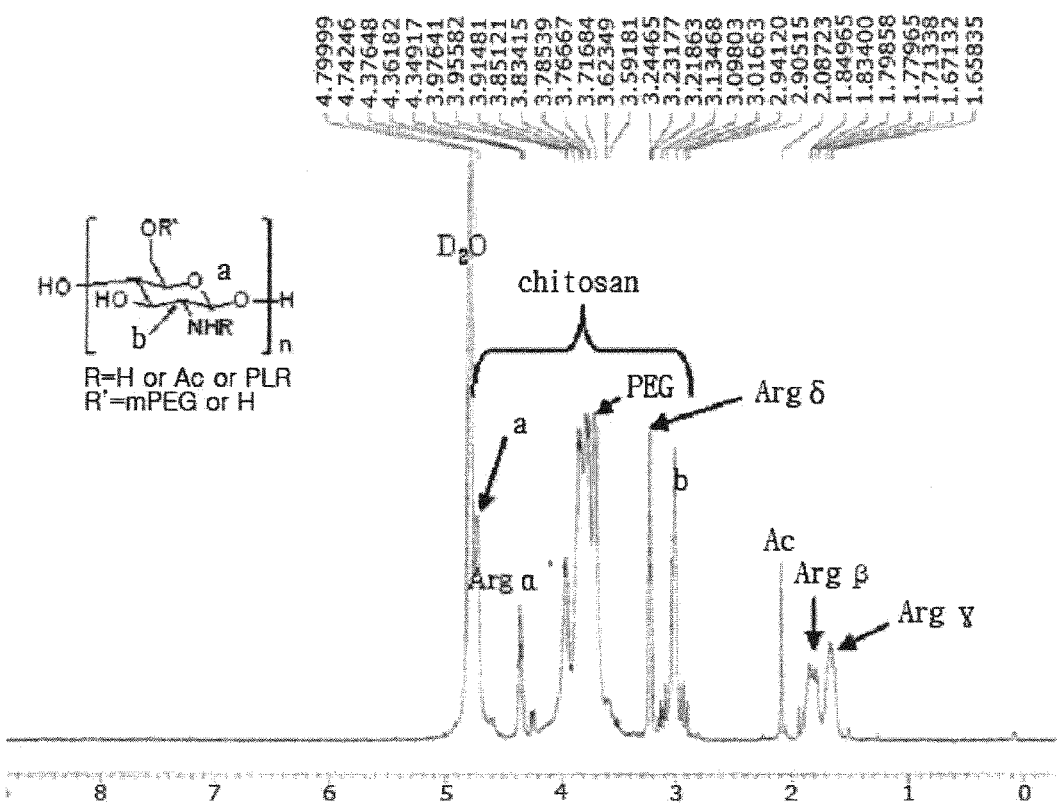
FIG. 5 shows the result of $^1$H NMR of 5'-mPEG2K-chitosan-polyarginine conjugate.

In order to achieve the objects, in one embodiment, the present invention provides a cationic polymer conjugate, prepared by covalently linking polyamine to an amine group of chitosan.

Chitosan is a general name of poly-[1,4]-β-D-glucosamine, and a basic polysaccharide generated through N-deacetylation by treating chitin, which is generally found in outer coat of insects including invertebrate Crustacea and cell wall of fungi, with the high concentration of alkali. The chitosan used in the present invention may be chemically derived from chitin or may be economically derived from widely available sources such as cell wall of fungi, outer coat of insects, in particular, Crustacea, and may be also commercially available.

Chitosans having different molecular weights may be used in the present invention, and chitosan having a molecular weight of 5,000 to 2,000,000 is preferred. In a specific embodiment, the present inventor used a low molecular weight-chitosan (LMW-chitosan; fw 50000~150000, Fluka, Swiss), a middle molecular weight-chitosan (MMW-chitosan; Aldrich, 190,000-310,000) and a high molecular weight-chitosan (HMW-chitosan; Aldrich, 310,000-375,000, or average molecular weight, 600,000 Fluka, Swiss) to prepare the chitosan based cationic polymer of the present invention.

In the present invention, any polyamine may used, as long as it has two or more amino groups in its molecule. Polyamine is commercially available or may be prepared by a known method in the related art. In a specific embodiment, the polyamine used in the present invention is positively charged, preferably a positively charged polyamino acid, and more preferably polyarginine, polyhistidine, or polylysine.

Further, the polyamine used in the present invention has a molecular weight of 500 to 300,000, and its molecular weight may vary depending on the type of polyamine.

In a specific embodiment, the present inventor used poly-L-arginine having a molecular weight of 15000 to 70000 or having a molecular weight of 70000 or more (Sigma, USA), poly-L-histidine having a molecular weight of 5000 (Sigma, USA), or poly-L-lysine having a molecular weight of 9200 (Sigma, USA) to prepare the conjugate of the present invention.

Upon binding reaction of chitosan and polyamine, a molar ratio of chitosan and polyamine is 1:1 to 1:10, and preferably 1:1 to 1:2. Upon binding reaction of chitosan, polyamine and polyethylene glycol, a molar ratio (%) of chitosan and polyethylene glycol is 1:1 to 1:50, and preferably 1:5 to 1:25.

In one preferred embodiment, polyethylene glycol may be additionally linked to the chitosan based cationic polymer conjugate of the present invention (that is, triple conjugate of chitosan, polyamine and polyethylene glycol).

The polyethylene glycol used in the present invention should be activated to bind with chitosan. The activation of biocompatible polymer such as polyethylene glycol is achieved by converting any one of terminal groups of the biocompatible polymer to a reactive group or moiety. The product by the modification is referred to as an "activated biocompatible polymer". For example, in order to bind a poly(alkyleneoxide) to a drug, one of hydroxyl terminal groups thereof can be converted to a reactive group such as carbonate, so as to give an activated poly(alkyleneoxide).

As a substantially non-antigenic polymer chain to be easily dissolved in various solvents, polyethylene glycol preferably has a number average molecular weight of about 300 to 100,000 daltons, and more preferably a number average molecular weight of about 1,000 to 20,000 daltons. The polyethylene glycol of the present invention may be a branched polyethylene glycol to bear a secondary or tertiary branched structure. Further, esters of bifunctional and hetero-bifunctional activated polyethylene glycol may be used.

Further, in one preferred embodiment, the polyethylene glycol used in the present invention may bind with an amino or hydroxy group of chitosan. In the present invention, in order to bind the polyethylene glycol to a specific functional group of chitosan, the amino or hydroxy group of chitosan is protected with a protecting material such as phthalic anhydride, and then polyethylene glycol is linked thereto.

Further, in one preferred embodiment, the chitosan based cationic polymer conjugate of the present invention may be additionally modified with a sugar moiety to facilitate the transfer of the conjugate into a target organ. Examples of the sugar moiety include mannose, galactose and glucose, but are not limited thereto. In a specific embodiment, the present inventor prepared a chitosan based cationic polymer, in which polyethylene glycol is modified with mannose.

In another preferred embodiment, the chitosan based cationic polymer conjugate of the present invention may be additionally associated with one or more gene medicines to be transferred in vivo, so as to form a complex. The gene medicine is preferably a plasmid DNA or small interfering RNA. In a specific embodiment, the present inventors prepared a complex of a chitosan-polyarginine conjugate or polyethylene glycol-chitosan-polyarginine conjugate with a survivin-specific small interfering RNA that inhibits the expression of mouse survivin. They found that in the case of transferring the complex in vivo, the gene transfer efficiency is improved, and cytotoxicity is significantly reduced, thereby effectively transferring and expressing the desired small interfering RNA in various cells.

Accordingly, the chitosan based polymer conjugate of the present invention forms a complex with a negatively charged gene such as plasmid DNA or small interfering RNA via electrostatic interaction, thereby being used as a gene delivery system for improving the gene transfer efficiency with low cytotoxicity.

Further, in still another embodiment, the present invention relates to a gene delivery composition for transferring gene medicines in vivo or a gene delivery composition for increasing the retention of gene medicines in blood, comprising the chitosan based cationic polymer conjugate.

The composition of the present invention may comprise the chitosan based cationic polymer conjugate of the present invention and additionally one or more gene medicines to be transferred in vivo. Preferably, the gene medicine is a plasmid DNA or small interfering RNA.

The term "administration", as used herein, means introduction of a predetermined amount of a substance into a patient by a certain suitable method. The composition of the present invention may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. In addition, the composition of the present invention may be administered using a certain apparatus capable of transporting the active ingredients into a target cell.

The composition of the present invention can further comprise a pharmaceutically acceptable carrier. For oral administration, the pharmaceutically acceptable carrier may include a binder, a lubricant, a disintegrator, an excipient, a solubilizer, a dispersing agent, a stabilizer, a suspending agent, a coloring agent, and a perfume. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The composition of the present invention may be formulated into a variety of dosage forms in combination with the aforementioned pharmaceutically acceptable carriers. For example, for oral administration, the composition may be formulated into tablets, troches, capsules, elixirs, suspensions, syrups or wafers. For injectable preparations, the pharmaceutical composition may be formulated into an ampule as a single-dose dosage form or a unit dosage form, such as a multidose container. The pharmaceutical composition may be also formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the formulations may further include fillers, anti-coagulating agents, lubricants, humectants, perfumes, and antiseptics.

The administration frequency and dose of the composition of the present invention can be determined by several related factors including the types of diseases to be treated, administration routes, the patient's age, gender, weight and severity of the illness, as well as by the types of the drug as an active component. Since the composition of the present invention has excellent duration of in-vivo efficacy and titer, it can remarkably reduce the administration frequency and dose. In the composition of the present invention, siRNA may be used in an amount of 0.1-500 pmole per weight (g) for systemic or topical administration, and plasmid DNA may be used in an amount of 0.1-1000 microgram per weight (g) for systemic or topical administration.

Further, in still another embodiment of the present invention, the present invention provides a method for preparing the chitosan based polymer conjugate of the present invention.

Specifically, the method of the present invention comprises a step of mixing chitosan with polyamine to conjugate with each other, preferably a step of stirring the mixture. To easily mix and conjugate chitosan with polyamine, a suitable solvent may be used to dissolve them. Any solvent can be used without limitation, as long as it can dissolve chitosan and polyamine. Depending on the use, the solvent may be suitably selected by those skilled in the art. Further, both materials may be readily mixed and conjugated with each other by stirring.

Further, in the present invention, to easily conjugate chitosan with polyamine, a coupling agent may be used for coupling a carboxyl group of terminal groups of chitosan or polyamine. Examples of the coupling agent include 1-ethyl-3-(3-dimethylamino-propyl)carbodiimide (EDAC), 1,3-diisopropylcarbodiimide (DIC), dicyclohexyl carbodiimide (DCC) and 1-ethyl-3-(3-dimethylamino propyl)-carbodiimide (EDC), and preferably EDAC.

Preferably, an auxiliary activating agent may be used with the coupling agent for a carboxyl group. Examples of the auxiliary activating agent include N-hydroxysuccinimide (NHS), 1-hydroxybenzotriazole (HOBt), 3,4-dihydro-3-hydroxy-4-oxo-1,2,3-benzotriazine (HOOBt), 1-hydroxy-7-azabenzotriazole (HOAt), and N-hydroxysulfosuccinimide (Sulfo-NHS), but are limited thereto.

The addition amounts of the coupling agent and auxiliary activating agent may be determined depending on various factors such as their activity and concentration. In a specific embodiment, chitosan is dissolved in a HCl solution to dilute the chitosan solution to a desired concentration, and then the solution is mixed with 1-ethyl-3-(3-dimethylamino-propyl) carbodiimide (EDAC), N-hydroxysulfosuccinimide (Sulfo-NHS), and polyamine, and then subjected to reaction under stirring for 24 hrs.

In a preferred embodiment, the preparation method of the present invention may further comprise a step of linking polyethylene glycol to chitosan. The polyethylene glycol used in the present invention should be activated for conjugation with chitosan, like the chitosan based cationic polymer conjugate. The activation of biocompatible polymers such as polyethylene glycol can be achieved by converting one of terminal groups of the biocompatible polymer to a reactive group or moiety. The polyethylene glycol may be conjugated with chitosan prior to conjugation of chitosan and polyamine, or after conjugation of chitosan and polyamine.

In still another embodiment, the preparation method of the present invention may further comprise a step of modifying the chitosan based cationic polymer with a sugar moiety.

In still another embodiment, the preparation method of the present invention may further comprise a step of forming a complex of the chitosan based cationic polymer and a desired gene medicine to be transferred in vivo. The desired gene medicine used for the complex formation is commercially available or prepared by a known method in the related art. More preferably, the gene medicine is a small interfering RNA or plasmid DNA. The complex formation may be performed by a known method in the related art. In the present invention, since the chitosan based cationic polymer is differently charged from the gene medicine, a simple treatment such as stirring is performed to form the complex.

In a specific embodiment, the present inventors determined a sequence of survivin-specific small interfering RNA that inhibits the expression of mouse survivin using a siRNA design program, and ordered. The small interfering RNA is mixed with a chitosan-polyarginine or chitosan-polyarginine-polyethylene glycol solution, and then left at 37° C. for 30 min to form a complex.

The products prepared in each step of the preparation method according to the present invention can be separated and/or purified from each reactant system by a known method in the related art. Examples of separation and purification include distillation (under atmospheric pressure or reduced pressure), recrystallization, column chromatography, ion-exchange chromatography, gel chromatography, affinity chromatography, thin layer chromatography, phase separation, solvent extraction, dialysis, and washing. Purification may be performed after each reaction or after a series of reactions.

As described above, the chitosan based cationic polymer conjugate produced by the preparation method of the present invention can improve in vivo transfer efficiency of negatively charged gene medicine such as plasmid DNA and small interfering RNA, and reduce cytotoxicity, thereby being used as a gene delivery system. In addition, the chitosan based cationic polymer conjugate can increase the retention of gene medicine in blood.

Accordingly, in still another embodiment, the present invention provides a method for using the chitosan based cationic polymer conjugate of the present invention as a delivery system for increasing the retention of gene medicine in blood. In order to use the conjugate of the present invention as a delivery system, the conjugate of the present invention may be administered alone or in a form of the composition comprising a pharmaceutically acceptable carrier. The administration method and dosage are the same as the above described in the composition of the present invention.

MODE FOR INVENTION

Hereinafter, the present invention will be described in detail with reference to Examples.

However, these Examples are for the illustrative purpose only, and the invention is not intended to be limited by these Examples.

Comparative Example 1

Preparation of Chitosan-Polyethylene Glycol Conjugate

A low molecular weight-chitosan (fw 50000~150000) was dissolved in a 0.1 M HCl solution at a concentration of 20 mg/ml, and then diluted with a PBS buffer solution (pH 7.4) at a concentration of 2 mg/ml.

5 ml of the prepared chitosan solution (fw 50000~150000, 10 mg, $6.2 \times 10^{-5}$ mol of pyranose units) was mixed with mPEG5k-SC (mPEG5k-succinyl carbonate, fw 5000, 24.84 mg, $4.96 \times 10^{-6}$ mol, 8 mol %, IDB, Korea), and then subjected to reaction under stirring at room temperature for 24 hrs. The mixture was purified using a centrifugal filter (MWCO 30k), and then freeze-dried to give a mPEG5k-LMW-chitosan conjugate (DP 8 mol %; DP: the degree of PEGylation).

Comparative Example 2

Preparation of Polyarginine-Polyethylene Glycol Conjugate 2 ml of 20 mM Tris buffer solution (pH 8.0) was mixed with poly-L-arginine (PLR; fw 15000~70000, 10 mg, $2.85 \times 10^{-7}$ mol, Sigma, USA) and mPEG5k-SC (fw 5000, 7.14 mg, $1.42 \times 10^{-6}$ mol), and then subjected to reaction under stirring at room temperature for 2 hrs. The mixture was purified using a centrifugal filter (MWCO 30k), and then freeze-dried to give a PEG-poly-L-arginine conjugate.

1. Preparation Method of Double Conjugate of Chitosan-Polyamine Polymer

Example 1

Preparation of LMW-chitosan-poly-L-arginine (fw 15000~70000) Conjugate 1-1. A Low molecular weight chitosan (LMW-chitosan; fw 50000~150000, Fluka, Swiss) was dissolved in a 0.1M HCl solution at a concentration of 20 mg/ml, and then diluted with a 50 mM MES buffer solution (pH 4.0) at a concentration of 2 mg/ml.

1-2. 1 ml of the chitosan solution prepared in Example 1-1 (fw 50000~150000, 2 mg, $1.24 \times 10^{-5}$ mol of pyranose units) was mixed with poly-L-arginine (PLR; fw 15000~70000, 0.7 mg, $0.2 \times 10^{-7}$ mol, Sigma, USA), 1-ethyl-3-(3-dimethylamino-propyl)carbodiimide (EDAC fw 191.7, 383.4 ug, $0.2 \times 10^{-5}$ mol), and N-hydroxysulfosuccinimide (Sulfo-NHS; fw 217.14, 434.28 ug, $0.2 \times 10^{-5}$ mol), and then subjected to reaction under stirring at room temperature for 24 hrs. The mixture was purified using a centrifugal filter (MWCO 30k, Sartorius, Germany), and then freeze-dried to give a LMW-chitosan-poly-L-arginine (fw 15000~70000) conjugate.

1-3. 1 ml of the chitosan solution prepared in Example 1-1 (fw 50000~150000, 2 mg, $1.24 \times 10^{-5}$ mol of pyranose units) was mixed with PLR (fw 15000~70000, 1.4 mg, $0.4 \times 10^{-7}$ mol), EDAC (fw 191.7, 766.8 ug, $0.4 \times 10^{-5}$ mol), and Sulfo-NHS (fw 217.14, 869 ug, $0.4 \times 10^{-5}$ mol), and then subjected to reaction under stirring at room temperature for 24 hrs. The mixture was purified using a centrifugal filter (MWCO 30k), and then freeze-dried to give a LMW-chitosan-poly-L-arginine (fw 15000~70000) conjugate.

1-4. 1 ml of the chitosan solution prepared in Example 1-1 (fw 50000~150000, 2 mg, $1.24 \times 10^{-5}$ mol of pyranose units) was mixed with PLR (fw 15000~70000, 3.5 mg, $1 \times 10^{-7}$ mol), EDAC (fw 191.7, 1.917 mg, $1 \times 10^{-5}$ mol), and Sulfo-NHS (fw 217.14, 2.17 mg, $1 \times 10^{-5}$ mol), and then subjected to reaction under stirring at room temperature for 24 hrs. The mixture was purified using a centrifugal filter (MWCO 30k), and then freeze-dried to give a LMW-chitosan-poly-L-arginine (fw 15000~70000) conjugate.

Example 2

Preparation of LMW-chitosan-poly-L-arginine (fw>70000) Conjugate 2-1. A LMW-chitosan-poly-L-arginine (fw>70000) conjugate was prepared in the same manner as in Example 1-2, except using PLR (fw>70000, 1.4 mg, $0.2 \times 10^{-7}$ mol, Sigma, USA) instead of PLR (fw 15000~70000).

2-2. A LMW-chitosan-poly-L-arginine (fw>70000) conjugate was prepared in the same manner as in Example 1-3, except using PLR (fw>70000, 2.8 mg, $0.4 \times 10^{-7}$ mol) instead of PLR (fw 15000~70000).

2-3. A LMW-chitosan-poly-L-arginine (fw>70000) conjugate was prepared in the same manner as in Example 1-4, except using PLR (fw>70000, 7 mg, $1 \times 10^{-7}$ mol) instead of PLR (fw 15000~70000).

Example 3

Preparation of LMW-chitosan-poly-L-histidine (fw 5000) Conjugate 3-1. A LMW-chitosan-poly-L-histidine (fw 5000) conjugate was prepared in the same manner as in Example 1-2, except using poly-L-histidine (PLH; fw 5000, 0.1 mg, $0.2 \times 10^{-7}$ mol, Sigma, USA) instead of PLR (fw 15000~70000).

3-2. A LMW-chitosan-poly-L-histidine (fw 5000) conjugate was prepared in the same manner as in Example 1-3, except using PLH (fw 5000, 0.2 mg, $0.4 \times 10^{-7}$ mol) instead of PLR (fw 15000~70000).

3-3. A LMW-chitosan-poly-L-histidine (fw 5000) conjugate was prepared in the same manner as in Example 1-4, except using PLH (fw 5000, 0.5 mg, $1\times10^{-7}$ mol) instead of PLR (fw 15000~70000).

Example 4

Preparation of LMW-chitosan-poly-L-lysine (fw 9200) Conjugate 4-1. A LMW-chitosan-poly-L-lysine (fw 9200) conjugate was prepared in the same manner as in Example 1-2, except using poly-L-lysine (PLK; fw 9200, 0.184 mg, $0.2\times10^{-7}$ mol, Sigma, USA) instead of PLR (fw 15000~70000).

4-2. A LMW-chitosan-poly-L-lysine (fw 9200) conjugate was prepared in the same manner as in Example 1-3, except using PLK (fw 9200, 0.368 mg, $0.4\times10^{-7}$ mol) instead of PLR (fw 15000~70000).

4-3. A LMW-chitosan-poly-L-lysine (fw 9200) conjugate was prepared in the same manner as in Example 1-4, except using PLK (fw 9200, 0.92 mg, $1\times10^{-7}$ mol) instead of PLR (fw 15000~70000).

Example 5

Preparation of MMW-chitosan-poly-L-arginine (fw 15000~70000) Conjugate 5-1. A chitosan solution was prepared using a medium molecular weight-chitosan (MMW-chitosan, Aldrich, USA) in the same manner as in Example 1-1.

5-2. A MMW-chitosan-poly-L-arginine (fw 15000~70000) conjugate was prepared using 1 ml of the chitosan solution prepared in Example 5-1 (2 mg, $1.24\times10^{-5}$ mol of pyranose units) in the same manner as in Example 1-2.

5-3. A MMW-chitosan-poly-L-arginine (fw 15000~70000) conjugate was prepared using 1 ml of the chitosan solution prepared in Example 5-1 (2 mg, $1.24\times10^{-5}$ mol of pyranose units) in the same manner as in Example 1-3.

5-4. A MMW-chitosan-poly-L-arginine (fw 15000~70000) conjugate was prepared using 1 ml of the chitosan solution prepared in Example 5-1 (2 mg, $1.24\times10^{-5}$ mol of pyranose units) in the same manner as in Example 1-4.

Example 6

Preparation of 14107-chitosan-poly-L-arginine (fw>70000) Conjugate 6-1. A MMW-chitosan-poly-L-arginine (fw>70000) conjugate was prepared using 1 ml of the chitosan solution prepared in Example 5-1 (2 mg, $1.24\times10^{-5}$ mol of pyranose units) and PLR (fw>70000, 1.4 mg, $0.2\times10^{-7}$ mol) in the same manner as in Example 1-2.

6-2. A MMW-chitosan-poly-L-arginine (fw>70000) conjugate was prepared using 1 ml of the chitosan solution prepared in Example 5-1 (2 mg, $1.24\times10^{-5}$ mol of pyranose units) and PLR (fw>70000, 2.8 mg, $0.4\times10^{-7}$ mol) in the same manner as in Example 1-3.

6-3. A MMW-chitosan-poly-L-arginine (fw>70000) conjugate was prepared using 1 ml of the chitosan solution prepared in Example 5-1 (2 mg, $1.24\times10^{-5}$ mol of pyranose units) and PLR (fw>70000, 7 mg, $1\times10^{-7}$ mol) in the same manner as in Example 1-4.

Example 7

Preparation of M/407-chitosan-poly-L-histidine (fw 5000) Conjugate 7-1. A MMW-chitosan-poly-L-histidine (fw 5000) conjugate was prepared using 1 ml of the chitosan solution prepared in Example 5-1 (2 mg, $1.24\times10^{-5}$ mol of pyranose units) and PLH (fw 5000, 0.1 mg, $0.2\times10^{-7}$ mol) in the same manner as in Example 1-2.

7-2. A MMW-chitosan-poly-L-histidine (fw 5000) conjugate was prepared using 1 ml of the chitosan solution prepared in Example 5-1 (2 mg, $1.24\times10^{-5}$ mol of pyranose units) and PLH (fw 5000, 0.2 mg, $0.4\times10^{-7}$ mol) in the same manner as in Example 1-3.

7-3. A MMW-chitosan-poly-L-histidine (fw 5000) conjugate was prepared using 1 ml of the chitosan solution prepared in Example 5-1 (2 mg, $1.24\times10^{-5}$ mol of pyranose units) and PLH (fw 5000, 0.5 mg, $1\times10^{-7}$ mol) in the same manner as in Example 1-4.

Example 8

Preparation of MMW-chitosan-poly-L-lysine (fw 9200) Conjugate 8-1. A MMW-chitosan-poly-L-lysine (fw 9200) conjugate was prepared using 1 ml of the chitosan solution prepared in Example 5-1 (2 mg, $1.24\times10^{-5}$ mol of pyranose units) and PLK (fw 9200, 0.184 mg, $0.2\times10^{-7}$ mol) in the same manner as in Example 1-2.

8-2. A MMW-chitosan-poly-L-lysine (fw 9200) conjugate was prepared using 1 ml of the chitosan solution prepared in Example 5-1 (2 mg, $1.24\times10^{-5}$ mol of pyranose units) and PLK (fw 9200, 0.368 mg, $0.4\times10^{-7}$ mol) in the same manner as in Example 1-3.

8-3. A MMW-chitosan-poly-L-lysine (fw 9200) conjugate was prepared using 1 ml of the chitosan solution prepared in Example 5-1 (2 mg, $1.24\times10^{-5}$ mol of pyranose units) and PLK (fw 9200, 0.92 mg, $1\times10^{-7}$ mol) in the same manner as in Example 1-4.

Example 9

Preparation of HMW-chitosan-poly-L-arginine (fw 15000~70000) Conjugate 9-1. A chitosan solution was prepared using a high molecular weight-chitosan (HMW-chitosan; fw ~600000, Fluka, Swiss) in the same manner as in Example 1-1.

9-2. A HMW-chitosan-poly-L-arginine (fw 15000~70000) conjugate was prepared using 1 ml of the chitosan solution prepared in Example 9-1 (fw ~600000, 2 mg, $1.24\times10^{-5}$ mol of pyranose units) in the same manner as in Example 1-2.

9-3. A HMW-chitosan-poly-L-arginine (fw 15000~70000) conjugate was prepared using 1 ml of the chitosan solution prepared in Example 9-1 (fw ~600000, 2 mg, $1.24\times10^{-5}$ mol of pyranose units) in the same manner as in Example 1-3.

9-4. A HMW-chitosan-poly-L-arginine (fw 15000~70000) conjugate was prepared using 1 ml of the chitosan solution prepared in Example 9-1 (fw ~600000, 2 mg, $1.24\times10^{-5}$ mol of pyranose units) in the same manner as in Example 1-4.

Example 10

Preparation of HMW-chitosan-poly-L-arginine (fw>70000) Conjugate 10-1. A HMW-chitosan-poly-L-arginine (fw>70000) conjugate was prepared using 1 ml of the chitosan solution prepared in Example 9-1 (fw ~600000, 2 mg, $1.24 \times 10^{-5}$ mol of pyranose units) and PLR (fw>70000, 1.4 mg, $0.2 \times 10^{-7}$ mol) in the same manner as in Example 1-2.

10-2. A HMW-chitosan-poly-L-arginine (fw>70000) conjugate was prepared using 1 ml of the chitosan solution prepared in Example 9-1 (fw ~600000, 2 mg, $1.24 \times 10^{-5}$ mol of pyranose units) and PLR (fw>70000, 2.8 mg, $0.4 \times 10^{-7}$ mol) in the same manner as in Example 1-3.

10-3. A HMW-chitosan-poly-L-arginine (fw>70000) conjugate was prepared using 1 ml of the chitosan solution prepared in Example 9-1 (fw ~600000, 2 mg, $1.24 \times 10^{-5}$ mol of pyranose units) and PLR (fw>70000, 7 mg, $1 \times 10^{-7}$ mol) in the same manner as in Example 1-4.

Example 11

Preparation of HMW-chitosan-poly-L-histidine (fw 5000) Conjugate 11-1. A HMW-chitosan-poly-L-histidine (fw 5000) conjugate was prepared using 1 ml of the chitosan solution prepared in Example 9-1 (fw ~600000, 2 mg, $1.24 \times 10^{-5}$ mol of pyranose units) and PLH (fw 5000, 0.1 mg, $0.2 \times 10^{-7}$ mol) in the same manner as in Example 1-2.

11-2. A HMW-chitosan-poly-L-histidine (fw 5000) conjugate was prepared using 1 ml of the chitosan solution prepared in Example 9-1 (fw ~600000, 2 mg, $1.24 \times 10^{-5}$ mol of pyranose units) and PLH (fw 5000, 0.2 mg, $0.4 \times 10^{-7}$ mol) in the same manner as in Example 1-3.

11-3. A HMW-chitosan-poly-L-histidine (fw 5000) conjugate was prepared using 1 ml of the chitosan solution prepared in Example 9-1 (fw ~600000, 2 mg, $1.24 \times 10^{-5}$ mol of pyranose units) and PLH (fw 5000, 0.5 mg, $1 \times 10^{-7}$ mol) in the same manner as in Example 1-4.

Example 12

Preparation of HMW-chitosan-poly-L-lysine (fw 9200) Conjugate 12-1. A HMW-chitosan-poly-L-lysine (fw 9200) conjugate was prepared using 1 ml of the chitosan solution prepared in Example 9-1 (fw ~600000, 2 mg, $1.24 \times 10^{-5}$ mol of pyranose units) and PLK (fw 9200, 0.184 mg, $0.2 \times 10^{-7}$ mol) in the same manner as in Example 1-2.

12-2. A HMW-chitosan-poly-L-lysine (fw 9200) conjugate was prepared using 1 ml of the chitosan solution prepared in Example 9-1 (fw ~600000, 2 mg, $1.24 \times 10^{-5}$ mol of pyranose units) and PLK (fw 9200, 0.368 mg, $0.4 \times 10^{-7}$ mol) in the same manner as in Example 1-3.

12-3. A HMW-chitosan-poly-L-lysine (fw 9200) conjugate was prepared using 1 ml of the chitosan solution prepared in Example 9-1 (fw ~600000, 2 mg, $1.24 \times 10^{-5}$ mol of pyranose units) and PLK (fw 9200, 0.92 mg, $1 \times 10^{-7}$ mol) in the same manner as in Example 1-4.

2. Preparation Method of Triple Conjugate of Polyethylene Glycol-Chitosan-Polyarginine

Example 13

Preparation of mPEG2k-LMW-chitosan-poly-L-arginine (fw 15000~70000) Conjugate 13-1. A LMW-chitosan (fw 50000~150000) was dissolved in 0.1M HCl solution at a concentration of 20 mg/ml, and then diluted with a PBS buffer solution (pH 7.4) at a concentration of 2 mg/ml.

13-2. 10% mPEG2k-LMW-chitosan-poly-L-arginine (fw 15000-70000) conjugate 10 ml of the chitosan solution prepared in Example 13-1 (fw 50000-450000, 20 mg, $1.24 \times 10^{-4}$ mol of pyranose units) was mixed with mPEG2k-SG (mPEG2k-succimidyl glutarate, fw 2000, 24.8 mg, $1.24 \times 10^{-5}$ mol, 10 mol %, IDB, Korea), and then subjected to reaction under stirring at room temperature for 24 hrs. The mixture was purified using a centrifugal filter (MWCO 30k), and then freeze-dried to give a mPEG2k-LMW-chitosan (fw 50000~150000) conjugate (DP 10 mol %; DP: the degree of PEGylation). 2 mg of the mPEG2k-LMW-chitosan (fw 50000~150000) conjugate was dissolved in 1 ml of 50 mM MES buffer solution (pH 4.0), and then mixed with (fw 15000~70000, PLR 0.7 mg, $0.2 \times 10^{-7}$ mol), EDAC (fw 191.7, 383.4 ug, $0.2 \times 10^{-5}$ mol), and Sulfo-NHS (fw 217.14, 434.28 ug, $0.2 \times 10^{-5}$ mol). The mixture was subjected to reaction under stirring at room temperature for 24 hrs. The mixture was purified using a centrifugal filter (MWCO 30k), and then freeze-dried to give a mPEG2k-LMW-chitosan-poly-L-arginine (fw 15000~70000) conjugate (DP 10 mol %).

13-3. 15% mPEG2k-LMW-chitosan-poly-L-arginine (fw 15000~70000) conjugate 10 ml of the chitosan solution prepared in Example 13-1 (fw 50000~150000, 20 mg, $1.24 \times 10^{-4}$ mol of pyranose units) was mixed with mPEG2k-SG (fw 2000, 37.26 mg, $1.863 \times 10^{-5}$ mol, 15 mol %), and then subjected to reaction under stirring at room temperature for 24 hrs. The mixture was purified using a centrifugal filter (MWCO 30k), and then freeze-dried to give a mPEG2k-LMW-chitosan (fw 50000~150000) conjugate (DP 15 mol %). 2 mg of the mPEG2k-LMW-chitosan (fw 50000~150000) conjugate was dissolved in 1 ml of 50 mM MES buffer solution (pH 4.0), and then mixed with PLR (fw 15000~70000, 0.7 mg, $0.2 \times 10^{-7}$ mol), EDAC (fw 191.7, 383.4 ug, $0.2 \times 10^{-5}$ mol), and Sulfo-NHS (fw 217.14, 434.28 ug, $0.2 \times 10^{-5}$ mol). The mixture was subjected to reaction under stirring at room temperature for 24 hrs. The mixture was purified using a centrifugal filter (MWCO 30k), and then freeze-dried to give a mPEG2k-LMW-chitosan-poly-L-arginine (fw 15000~70000) conjugate (DP 15 mol %).

Example 14

Preparation of mPEG2k-LMW-chitosan-PLR (fw>70000) Conjugate 14-1. 10% mPEG2k-LMW-chitosan-poly-L-arginine (fw>70000) conjugate A mPEG2k-LMW-chitosan-poly-L-arginine (fw>70000) conjugate (DP 10 mol %) was prepared in the same manner as in Example 13-2, except using PLR (fw>70000, 1.4 mg, $0.2 \times 10^{-7}$ mol) instead of PLR (fw 15000~70000).

14-2. 15% mPEG2k-LMW-chitosan-poly-L-arginine (fw>70000) conjugate

A mPEG2k-LMW-chitosan-PLR (fw>70000) conjugate (DP 15 mol %) was prepared in the same manner as in Example 13-3, except using PLR (fw>70000, 1.4 mg, 0.2×$10^{-7}$ mol) instead of PLR (fw 15000~70000).

Example 15

Preparation of mPEG2k-LMW-chitosan-poly-L-histidine (fw 5000) Conjugate 15-1. 10% mPEG2k-LMW-chitosan-poly-L-histidine (fw 5000) conjugate A mPEG2k-LMW-chitosan-poly-L-histidine (fw 5000) conjugate (DP 10 mol %) was prepared in the same manner as in Example 13-2, except using PLH (fw 5000, 0.1 mg, 0.2×$10^{-7}$ mol) instead of PLR (fw 15000~70000).

15-2. 15% mPEG2k-LMW-chitosan-poly-L-histidine (fw 5000) conjugate

A mPEG2k-LMW-chitosan-poly-L-histidine (fw 5000) conjugate (DP 15 mol %) was prepared in the same manner as in Example 13-3, except using PLH (fw 5000, 0.1 mg, 0.2×$10^{-7}$ mol) instead of PLR (fw 15000~70000).

Example 16

Preparation of mPEG2k-LMW-chitosan-poly-L-lysine (fw 9200) Conjugate 16-1. 10% mPEG2k-LMW-chitosan-poly-L-lysine (fw 9200) conjugate A mPEG2k-LMW-chitosan-poly-L-lysine (fw 9200) conjugate (DP 10 mol %) was prepared in the same manner as in Example 13-2, except using PLK (fw 9200, 0.184 mg, 0.2×$10^{-7}$ mol) instead of PLR (fw 15000~70000).

16-2. 15% mPEG2k-LMW-chitosan-poly-L-lysine (fw 9200) conjugate

A mPEG2k-LMW-chitosan-poly-L-lysine (fw 9200) conjugate (DP 15 mol %) was prepared in the same manner as in Example 13-3, except using PLK (fw 9200, 0.184 mg, 0.2×$10^{-7}$ mol) instead of PLR (fw 15000~70000).

Example 17

Preparation of mPEG2k-MMW-chitosan-poly-L-arginine (fw 15000~70000) Conjugate 17-1. A chitosan solution was prepared using a MMW-chitosan in the same manner as in Example 13-1.

17-2. 10% mPEG2k-MMW-chitosan-poly-L-arginine (fw 15000~70000) conjugate

A mPEG2k-MMW-chitosan-poly-L-arginine (fw 15000~70000) conjugate (DP 10 mol %) was prepared using 10 ml of the chitosan solution prepared in 17-1 (20 mg, 1.24×$10^{-4}$ mol of pyranose units) in the same manner as in Example 13-2.

17-3. 15% mPEG2k-MMW-chitosan-poly-L-arginine (fw 15000~70000) conjugate

A mPEG2k-MMW-chitosan-poly-L-arginine (fw 15000~70000) conjugate (DP 15 mol %) was prepared using 10 ml of the chitosan solution prepared in 17-1 (20 mg, 1.24×$10^{-4}$ mol of pyranose units) in the same manner as in Example 13-3.

Example 18

Preparation of mPEG2k-MMW-chitosan-poly-L-arginine (fw>70000) Conjugate 18-1. Preparation of 10% mPEG2k-MMW-chitosan-poly-L-arginine (fw>70000) conjugate A mPEG2k-MMW-chitosan-PLR (fw>70000) conjugate (DP 10 mol %) was prepared using 10 ml of the chitosan solution prepared in Example 17-1 (20 mg, 1.24×$10^{-4}$ mol of pyranose units) and PLR (fw>70000, 1.4 mg, 0.2×$10^{-7}$ mol) in the same manner as in Example 13-2.

18-2. Preparation of 15% mPEG2k-MMW-chitosan-poly-L-arginine (fw>70000) conjugate A mPEG2k-MMW-chitosan-poly-L-arginine (fw>70000) conjugate (DP 15 mol %) was prepared using 10 ml of the chitosan solution prepared in Example 17-1 (20 mg, 1.24×$10^{-4}$ mol of pyranose units) and PLR (fw>70000, 1.4 mg, 0.2×$10^{-7}$ mol) in the same manner as in Example 13-3.

Example 19

Preparation of mPEG2k-MMW-chitosan-poly-L-histidine (fw 5000) Conjugate 19-1. 10% mPEG2k-MMW-chitosan-poly-L-histidine (fw 5000) conjugate A mPEG2k-MMW-chitosan-poly-L-histidine (fw 5000) conjugate (DP 10 mol %) was prepared using 10 ml of the chitosan solution prepared in Example 17-1 (20 mg, 1.24×$10^{-4}$ mol of pyranose units) and PLH (fw 5000, 0.1 mg, 0.2×$10^{-7}$ mol) in the same manner as in Example 13-2.

19-2. 15% mPEG2k-MMW-chitosan-poly-L-histidine (fw 5000) conjugate

A mPEG2k-MMW-chitosan-poly-L-histidine (fw 5000) conjugate (DP 15 mol %) was prepared using 10 ml of the chitosan solution prepared in Example 17-1 (20 mg, 1.24×$10^{-4}$ mol of pyranose units) and PLH (fw 5000, 0.1 mg, 0.2×$10^{-7}$ mol) in the same manner as in Example 13-3.

Example 20

Preparation of mPEG2k-MMW-chitosan-poly-L-lysine (fw 9200) Conjugate 20-1. 10% mPEG2k-MMW-chitosan-poly-L-lysine (fw 9200) conjugate A mPEG2k-MMW-chitosan-poly-L-lysine (fw 9200) conjugate (DP 10 mol %) was prepared using 10 ml of the chitosan solution prepared in Example 17-1 (20 mg, 1.24×$10^{-4}$ mol of pyranose units) and PLK (fw 5000, 0.184 mg, 0.2×$10^{-7}$ mol) in the same manner as in Example 13-2.

20-2. 15% mPEG2k-MMW-chitosan-poly-L-lysine (fw 9200) conjugate

A mPEG2k-MMW-chitosan-poly-L-lysine (fw 9200) conjugate (DP 15 mol %) was prepared using 10 ml of the chitosan solution prepared in Example 17-1 (20 mg, 1.24×$10^{-4}$ mol of pyranose units) and PLK (fw 5000, 0.184 mg, 0.2×$10^{-7}$ mol) in the same manner as in Example 13-3.

Example 21

Preparation of mPEG2k-HMW-chitosan-poly-L-arginine (fw 15000~70000) Conjugate 21-1. A chitosan solution was prepared using a HMW-chitosan (fw ~600000) in the same manner as in Example 13-1.

21-2. 10% mPEG2k-HMW-chitosan-poly-L-arginine (fw 15000~70000) conjugate

A mPEG2k-HMW-chitosan-poly-L-arginine (fw 15000~70000) conjugate (DP 10 mol %) was prepared using 10 ml of the chitosan solution prepared in Example 21-1 (20 mg, $1.24 \times 10^{-4}$ mol of pyranose units) in the same manner as in Example 13-2.

21-3. 15% mPEG2k-HMW-chitosan-poly-L-arginine (fw 15000~70000) conjugate

A mPEG2k-HMW-chitosan-poly-L-arginine (fw 15000~70000) conjugate (DP 15 mol %) was prepared using 10 ml of the chitosan solution prepared in Example 21-1 (20 mg, $1.24 \times 10^{-4}$ mol of pyranose units) in the same manner as in Example 13-3.

Example 22

Preparation of mPEG2k-HMW-chitosan-poly-L-arginine (fw>70000) Conjugate 22-1. 10% mPEG2k-HMW-chitosan-poly-L-arginine (fw>70000) conjugate A mPEG2k-HMW-chitosan-poly-L-arginine (fw>70000) conjugate (DP 10 mol %) was prepared using 10 ml of the chitosan solution prepared in Example 21-1 (20 mg, $1.24 \times 10^{-4}$ mol of pyranose units) and PLR (fw>70000, 1.4 mg, $0.2 \times 10^{-7}$ mol) in the same manner as in Example 13-2.

22-2. 15% mPEG2k-HMW-chitosan-poly-L-arginine (fw>70000) Conjugate

A mPEG2k-HMW-chitosan-poly-L-arginine (fw>70000) conjugate was prepared using 10 ml of the chitosan solution prepared in Example 21-1 (20 mg, $1.24 \times 10^{-4}$ mol of pyranose units) and PLR (fw>70000, 1.4 mg, $0.2 \times 10^{-7}$ mol) in the same manner as in Example 13-3.

Example 23

Preparation of mPEG2k-HMW-chitosan-poly-L-histidine (fw 5000) Conjugate 23-1. 10% mPEG2k-HMW-chitosan-poly-L-histidine (fw 5000) conjugate A mPEG2k-HMW-chitosan-poly-L-histidine (fw 5000) conjugate (DP 10 mol %) was prepared using 10 ml of the chitosan solution prepared in Example 21-1 (20 mg, $1.24 \times 10^{-4}$ mol of pyranose units) and PLH (fw 5000, 0.1 mg, $0.2 \times 10^{-7}$ mol) in the same manner as in Example 13-2.

23-2. 15% mPEG2k-HMW-chitosan-poly-L-histidine (fw 5000) conjugate

A mPEG2k-HMW-chitosan-poly-L-histidine (fw 5000) conjugate (DP 15 mol %) was prepared using 10 ml of the chitosan solution prepared in Example 21-1 (20 mg, $1.24 \times 10^{-4}$ mol of pyranose units) and PLH (fw 5000, 0.1 mg, $0.2 \times 10^{-7}$ mol) in the same manner as in Example 13-3.

Example 24

Preparation of mPEG2k-HMW-chitosanpoly-L-lysine (fw 9200) Conjugate 24-1. 10% mPEG2k-HMW-chitosan-poly-L-lysine (fw 9200) conjugate A mPEG2k-HMW-chitosan-poly-L-lysine (fw 9200) conjugate (DP 10 mol %) was prepared using 10 ml of the chitosan solution prepared in Example 21-1 (20 mg, $1.24 \times 10^{-4}$ mol of pyranose units) and PLK (fw 5000, 0.184 mg, $0.2 \times 10^{-7}$ mol) in the same manner as in Example 13-2.

24-2. 15% mPEG2k-HMW-chitosan-poly-L-lysine (fw 9200) conjugate

A mPEG2k-HMW-chitosan-poly-L-lysine (fw 9200) conjugate (DP 15 mol %) was prepared using 10 ml of the chitosan solution prepared in Example 21-1 (20 mg, $1.24 \times 10^{-4}$ mol of pyranose units) and PLK (fw 5000, 0.184 mg, $0.2 \times 10^{-7}$ mol) in the same manner as in Example 13-3.

Example 25

Preparation of mPEG5k-LMW-chitosan-poly-L-arginine (fw 15000~70000) Conjugate 25-1. 5% mPEG5k-LMW-chitosan-poly-L-arginine (fw 15000~70000) conjugate 10 ml of the chitosan solution prepared in Example 13-1 (fw 50000~150000, 20 mg, $1.24 \times 10^{-4}$ mol of pyranose units) and mPEG5k-SC (fw 5000, 31.05 mg, $6.21 \times 10^{-6}$ mol, 5 mol %, IDB, Korea) were mixed together, and then subjected to reaction under stirring at room temperature for 24 hrs. The mixture was purified using a centrifugal filter (MWCO 30k), and then freeze-dried to give a mPEG5k-LMW-chitosan (fw 50000~150000) conjugate (DP 5 mol %). 2 mg of the prepared mPEG5k-LMW-chitosan (fw 50000~150000) conjugate was dissolved in 1 ml of 50 mM MES buffer solution (pH 4.0), and then mixed with PLR (fw 15000~70000, 0.7 mg, $0.2 \times 10^{-7}$ mol), EDAC (fw 191.7, 386.4 ug, $0.2 \times 10^{-5}$ mol), and Sulfo-NHS (fw 217.14, 434.28 ug, $0.2 \times 10^{-5}$ mol), followed by stirring at room temperature for 24 hrs. The mixture was purified using a centrifugal filter (MWCO 30k), and then freeze-dried to give a mPEG5k-LMW-chitosan-poly-L-arginine (fw 15000~70000) conjugate (DP 5 mol %).

25-2. 15% mPEG5k-LMW-chitosan-poly-L-arginine (fw 15000-70000) conjugate 10 ml of the chitosan solution prepared in Example 13-1 (fw 50000~150000, 20 mg, $1.24 \times 10^{-4}$ mol of pyranose units) and mPEG5k-SC (fw 5000, 46.58 mg, $9.316 \times 10^{-6}$ mol, 15 mol %) were mixed together, and then subjected to reaction under stirring at room temperature for 24 hrs. The mixture was purified using a centrifugal filter (MWCO 30k), and then freeze-dried to give a mPEG5k-LMW-chitosan (fw 50000~150000) conjugate (DP 15 mol %). 2 mg of the prepared mPEG5k-LMW-chitosan (fw 50000~150000) conjugate was dissolved in 1 ml of 50 mM MES buffer solution (pH 4.0), and then mixed with PLR (fw 15000~70000, 0.7 mg, $0.2 \times 10^{-7}$ mol), EDAC (fw 191.7, 386.4 ug, $0.2 \times 10^{-5}$ mol), and Sulfo-NHS (fw 217.14, 434.28 ug. $0.4 \times 10^{-5}$ mol), followed by stirring at room temperature for 24 hrs. The mixture was purified using a centrifugal filter (MWCO 30k), and then freeze-dried to give a mPEG5k-LMW-chitosan-poly-L-arginine (fw 15000~70000) conjugate (DP 15 mol %).

Example 26

Preparation of mPEG5k-LMW-chitosan-PLR (fw>70000) Conjugate 26-1. 5% mPEG5k-LMW-chitosan-PLR (fw>70000) conjugate A mPEG5k-LMW-chitosan-poly-L-arginine (fw>70000) conjugate (DP 5 mol %) was prepared in the same manner as in Example 25-1, except using PLR (fw>70000, 1.4 mg, $0.2 \times 10^{-7}$ mol) instead of PLR (fw 15000~70000).

26-2. 15% mPEG5k-LMW-chitosan-PLR (fw>70000) conjugate

A mPEG5k-LMW-chitosan-poly-L-arginine (fw>70000) conjugate (DP 15 mol %) was prepared in the same manner as in Example 25-2, except using PLR (fw>70000, 1.4 mg, $0.2 \times 10^{-7}$ mol) instead of PLR (fw 15000~70000).

Example 27

Preparation of mPEG5k-LMW-chitosan-poly-L-histidine (fw 5000) Conjugate 27-1. 5% mPEG5k-LMW-chitosan-poly-L-histidine (fw 5000) conjugate A mPEG5k-LMW-chitosan-poly-L-histidine (fw 5000) conjugate (DP 5 mol %) was prepared in the same manner as in Example 25-1, except using PLH (fw 5000, 0.1 mg, $0.2 \times 10^{-7}$ mol) instead of PLR (fw 15000~70000).

27-2. 15% mPEG5k-LMW-chitosan-poly-L-histidine (fw 5000) conjugate

A mPEG5k-LMW-chitosan-poly-L-histidine (fw 5000) conjugate (DP 15 mol %) was prepared in the same manner as in Example 25-2, except using PLH (fw 5000, 0.1 mg, $0.2 \times 10^{-7}$ mol) instead of PLR (fw 15000~70000).

Example 28

Preparation of mPEG5k-LMW-chitosan-poly-L-lysine (fw 9200) Conjugate 28-1. 5% mPEG5k-LMW-chitosan-poly-L-lysine (fw 9200) conjugate A mPEG5k-LMW-chitosan-poly-L-lysine (fw 9200) conjugate (DP 5 mol %) was prepared in the same manner as in Example 25-1, except using PLK (fw 9200, 0.184 mg, $0.2 \times 10^{-7}$ mol) instead of PLR (fw 15000~70000).

28-2. 15% mPEG5k-LMW-chitosan-poly-L-lysine (fw 9200) conjugate

A mPEG5k-LMW-chitosan-poly-L-lysine (fw 9200) conjugate (DP 15 mol %) was prepared in the same manner as in Example 25-2, except using PLK (fw 9200, 0.184 mg, $0.2 \times 10^{-7}$ mol) instead of PLR (fw 15000~70000).

Example 29

Preparation of mPEG5k-MMW-chitosan-poly-L-arginine (fw 15000~70000) Conjugate 29-1. 5% mPEG5k-MMW-chitosan-poly-L-arginine (fw 15000~70000) conjugate A mPEG5k-MMW-chitosan-poly-L-arginine (fw 15000~70000) conjugate (DP 5 mol %) was prepared using 10 ml of the chitosan solution prepared in Example 17-1 (20 mg, $1.24 \times 10^{-4}$ mol of pyranose units) in the same manner as in Example 25-1.

29-2. 15% mPEG5k-MMW-chitosan-poly-L-arginine (fw 15000~70000) conjugate

A mPEG5k-MMW-chitosan-poly-L-arginine (fw 15000~70000) conjugate (DP 15 mol %) was prepared using 10 ml of the chitosan solution prepared in Example 17-1 (20 mg, $1.24 \times 10^{-4}$ mol of pyranose units) in the same manner as in Example 25-2.

Example 30

Preparation of mPEG5k-MMW-chitosan-poly-L-arginine (fw>70000) Conjugate 30-1. 5% mPEG5k-MMW-chitosan-poly-L-arginine (fw>70000) conjugate A mPEG5k-MMW-chitosan-poly-L-arginine (fw>70000) conjugate (DP 5 mol %) was prepared using 10 ml of the chitosan solution prepared in Example 17-1 (20 mg, $1.24 \times 10^{-4}$ mol of pyranose units) and PLR (fw>70000, 1.4 mg, $0.2 \times 10^{-7}$ mol) in the same manner as in Example 25-1.

30-2. 15% mPEG5k-MMW-chitosan-poly-L-arginine (fw>70000) conjugate

A mPEG5k-MMW-chitosan-poly-L-arginine (fw>70000) conjugate (DP 15 mol %) was prepared using 10 ml of the chitosan solution prepared in Example 17-1 (20 mg, $1.24 \times 10^{-4}$ mol of pyranose units) and PLR (fw>70000, 1.4 mg, $0.2 \times 10^{-7}$ mol) in the same manner as in Example 25-2.

Example 31

Preparation of mPEG5k-MMW-chitosan-poly-L-histidine (fw 5000) Conjugate 31-1. 5% mPEG5k-MMW-chitosan-poly-L-histidine (fw 5000) conjugate A mPEG5k-MMW-chitosan-poly-L-histidine (fw 5000) conjugate (DP 5 mol %) was prepared using 10 ml of the chitosan solution prepared in Example 17-1 (20 mg, $1.24 \times 10^{-4}$ mol of pyranose units) and PLH (fw 5000, 0.1 mg, $0.2 \times 10^{-7}$ mol) in the same manner as in Example 25-1.

31-2. 15% mPEG5k-MMW-chitosan-poly-L-histidine (fw 5000) conjugate

A mPEG5k-MMW-chitosan-poly-L-histidine (fw 5000) conjugate (DP 15 mol %) was prepared using 10 ml of the chitosan solution prepared in Example 17-1 (20 mg, $1.24 \times 10^{-4}$ mol of pyranose units) and PLH (fw 5000, 0.1 mg, $0.2 \times 10^{-7}$ mol) in the same manner as in Example 25-2.

Example 32

Preparation of mPEG5k-MMW-chitosan-poly-L-lysine (fw 9200) Conjugate 32-1. 5% mPEG5k-MMW-chitosan-poly-L-lysine (fw 9200) conjugate A mPEG5k-MMW-chitosan-poly-L-lysine (fw 9200) conjugate (DP 5 mol %) was prepared using 10 ml of the chitosan solution prepared in Example 17-1 (20 mg, $1.24 \times 10^{-4}$ mol of pyranose units) and PLK (fw 9200, 0.184 mg, $0.2 \times 10^{-7}$ mol) in the same manner as in Example 25-1.

32-2. 15% mPEG5k-MMW-chitosan-poly-L-lysine (fw 9200) conjugate

A mPEG5k-MMW-chitosan-poly-L-lysine (fw 9200) conjugate (DP 15 mol %) was prepared using 10 ml of the chitosan solution prepared in Example 17-1 (20 mg, 1.24×$10^{-4}$ mol of pyranose units) and PLK (fw 9200, 0.184 mg, 0.2×$10^{-7}$ mol) in the same manner as in Example 25-2.

Example 33

Preparation of mPEG5k-HMW-chitosan-poly-L-arginine (fw 15000~70000) Conjugate 33-1. 5% mPEG5k-HMW-chitosan-poly-L-arginine (fw 15000~70000) conjugate A mPEG5k-HMW-chitosan-poly-L-arginine (fw 15000~70000) conjugate (DP 5 mol %) was prepared using 10 ml of the chitosan solution prepared in Example 21-1 (20 mg, 1.24×$10^{-4}$ mol of pyranose units) in the same manner as in Example 25-1.

33-2. 15% mPEG5k-HMW-chitosan-poly-L-arginine (fw 15000-70000) conjugate

A mPEG5k-HMW-chitosan-poly-L-arginine (fw 15000~70000) conjugate (DP 15 mol %) was prepared using 10 ml of the chitosan solution prepared in Example 21-1 (20 mg, 1.24×$10^{-4}$ mol of pyranose units) in the same manner as in Example 25-2.

Example 34

Preparation of mPEG5k-HMW-chitosan-PLR (fw>70000) Conjugate 34-1. 5% mPEG5k-HMW-chitosan-PLR (fw>70000) conjugate A mPEG5k-HMW-chitosan-poly-L-arginine (fw>70000) conjugate (DP 5 mol %) was prepared using 10 ml of the chitosan solution prepared in Example 21-1 (20 mg, 1.24×$10^{-4}$ mol of pyranose units) and PLR (fw>70000, 1.4 mg, 0.2×$10^{-7}$ mol) in the same manner as in Example 25-1.

34-2. 15% mPEG5k-HMW-chitosan-PLR (fw>70000) conjugate

A mPEG5k-HMW-chitosan-poly-L-arginine (fw>70000) conjugate (DP 15 mol %) was prepared using 10 ml of the chitosan solution prepared in Example 21-1 (20 mg, 1.24×$10^{-4}$ mol of pyranose units) and PLR (fw>70000, 1.4 mg, 0.2×$10^{-7}$ mol) in the same manner as in Example 25-2.

Example 35

Preparation of mPEG5k-HMW-chitosan-poly-L-histidine (fw 5000) Conjugate 35-1. 5% mPEG5k-HMW-chitosan-poly-L-histidine (fw 5000) conjugate A mPEG5k-HMW-chitosan-poly-L-histidine (fw 5000) conjugate (DP 5 mol %) was prepared using 10 ml of the chitosan solution prepared in Example 21-1 (20 mg, 1.24×$10^{-4}$ mol of pyranose units) and PLH (fw 5000, 0.1 mg, 0.2×$10^{-7}$ mol) in the same manner as in Example 25-1.

35-2. 15% mPEG5k-HMW-chitosan-poly-L-histidine (fw 5000) conjugate

A mPEG5k-HMW-chitosan-poly-L-histidine (fw 5000) conjugate (DP 15 mol %) was prepared using 10 ml of the chitosan solution prepared in Example 21-1 (20 mg, 1.24×$10^{-4}$ mol of pyranose units) and PLH (fw 5000, 0.1 mg, 0.2×$10^{-7}$ mol) in the same manner as in Example 25-2.

Example 36

Preparation of mPEG5k-HMW-chitosan-poly-L-lysine (fw 9200) Conjugate 36-1. 5% mPEG5k-HMW-chitosan-poly-L-lysine (fw 9200) conjugate A mPEG5k-HMW-chitosan-poly-L-lysine (fw 9200) conjugate (DP 5 mol %) was prepared using 10 ml of the chitosan solution prepared in Example 21-1 (20 mg, 1.24×$10^{-4}$ mol of pyranose units) and PLK (fw 9200, 0.184 mg, 0.2×$10^{-7}$ mol) in the same manner as in Example 25-1.

36-2. 15% mPEG5k-HMW-chitosan-poly-L-lysine (fw 9200) conjugate

A mPEG5k-HMW-chitosan-poly-L-lysine (fw 9200) conjugate (DP 15 mol %) was prepared using 10 ml of the chitosan solution prepared in Example 21-1 (20 mg, 1.24×$10^{-4}$ mol of pyranose units) and PLK (fw 9200, 0.184 mg, 0.2×$10^{-7}$ mol) in the same manner as in Example 25-2.

Example 37

Preparation of 5'-mPEG2k-LMW-chitosan-poly-L-arginine (fw 15000~70000) Conjugate 37-1. Preparation of mPEG2K—COCH($CH_3$)Cl mPEG2K—OH (0.5 g, 0.25 mmol), 4-dimethylaminopyridine (DMAP; 91.6 mg, 0.75 mmol), and triethylamine (TEA; 0.070 ml, 0.5 mmol) were dissolved in 12 ml of dichloromethane (DCM), and then slowly added to a solution of 2-chloropropionyl chloride (0.12 ml, 1.25 mmol) dissolved in 3 ml of DCM at 0° C. under nitrogen gas, and then the reaction temperature was raised from 0° C. to room temperature, followed by stirring for 24 hrs. The reaction was confirmed by TLC. The reaction mixture was concentrated under reduced pressure, and precipitated in diethyl ether, filtered, and purified. The resultant was recrystallized in ethanol, filtered, and purified. The structure of the compound was confirmed by 500 MHz 1H-NMR.

37-2. Preparation of Phthaloyl LMW Chitosan (phth-LMW-chitosan)

A LMW-chitosan (LMW-Chitosan Fluka, 500 mg, 3.1 mmol) and phthalic anhydride (Phthalic anhydride 1.38 g, 9.32 mmol) were dissolved in 10 ml of dimethylformamide (DMF), and the solution was heated to 130° C. under nitrogen gas, followed by stirring for 7 hrs. The reactant was cooled to room temperature, and the precipitate was washed with ice water, and filtered. The resulting solid was purified with ethanol by soxhlet extraction. The resulting solid was dried under vacuum at 50° C. to give a phth-LMW-chitosan having a protected amine group of chitosan.

37-3. Preparation of 15 mol % PEGylated 5'-mPEG2K-LMW-chitosan

A phth-LMW-chitosan (70 mg, 0.24 mmol) prepared in Example 37-2 was dissolved in 1 ml of pyridine, and the solution mixed with a solution of mPEG2K—COCH($CH_3$)Cl (72.2 mg, 36.1 µmol) prepared in Example 37-1 in 2 ml of DMF. The mixture was heated to 100° C. under nitrogen gas, followed by stirring for 24 hrs. The reactant was cooled to room temperature, and precipitated in ethanol. The resultant was washed with ethanol and ether, and filtered. The resulting solid 5'-mPEG2K-chitosan (phth), in which 5'C hydroxy group of chitosan was conjugated with PEG, was dried under vacuum. 50 mg of 5'-mPEG2K-chitosan (phth) was dissolved in 10 ml of hydrazine monohydrate ($H_2NNH_2 \cdot H_2O$), and the solution was refluxed under nitrogen gas at 130° C., while stirring for 24 hrs. The reactant was cooled to room temperature. The precipitate was purified, and mixed with 10 ml of 0.1 M NaOH (aq), followed by stirring at room temperature for 16 hrs. The pH of the mixture was adjusted to 10 with 50 mM HCl (aq) by dialysis, and freeze-dried to give a compound 5'-mPEG2K-LMW-chitosan. The compound was confirmed by 500 MHz 1H-NMR.

37-4. Preparation of 10 mol % PEGylated 5'-mPEG2K-LMW-chitosan 10 mol % PEGylated 5'-mPEG2K-LMW-chitosan was prepared using mPEG2K—COCH(CH$_3$)Cl (48.1 mg, 24.0 mmol) in the same manner as in Example 37-3.

37-5. 15% 5'-mPEG2k-LMW-chitosan-poly-L-arginine (fw 15000~70000)

2 mg of 5'-mPEG2K-LMW-chitosan prepared in Example 37-3 was dissolved in 1 ml of 50 mM MES buffer solution (pH 4.0), and then mixed with PLR (fw 15000~70000, 0.7 mg, $0.2 \times 10^{-7}$ mol), EDAC (fw 191.7, 383.4 ug, $0.2 \times 10^{-5}$ mol), and Sulfo-NHS (fw 217.14, 434.28 ug, $0.2 \times 10^{-5}$ mol), followed by stirring at room temperature for 24 hrs. The mixture was purified using a centrifugal filter (MWCO 30k), and then freeze-dried to give a 5'-mPEG2k-LMW-chitosan-poly-L-arginine (fw 15000~70000) conjugate.

37-6 10% 5'-mPEG2k-LMW-chitosan-poly-L-arginine (fw 15000~70000)

2 mg of 5'-mPEG2K-LMW-chitosan prepared in Example 37-4 was dissolved in 1 ml of 50 mM MES buffer solution (pH 4.0), and then mixed with PLR (fw 15000~70000, 0.7 mg, $0.2 \times 10^{-7}$ mol), EDAC (fw 191.7, 383.4 ug, $0.2 \times 10^{-5}$ mol), and Sulfo-NHS (fw 217.14, 434.28 ug, $0.2 \times 10^{-5}$ mol), followed by stirring at room temperature for 24 hrs. The mixture was purified using a centrifugal filter (MWCO 30k), and then freeze-dried to give a 5'-mPEG2k-LMW-chitosan-poly-L-arginine (fw 15000~70000) conjugate.

Example 38

Preparation of 5'-mPEG2k-LMW-chitosan-poly-L-arginine (fw>70000) Conjugate 38-1. 15% 5'-mPEG2k-LMW-chitosan-poly-L-arginine (fw>70000)

A 5'-mPEG2k-LMW-chitosan-poly-L-arginine (fw>70000) conjugate was prepared in the same manner as in Example 37-5, except using PLR (fw>70000, 1.4 mg, $0.2 \times 10^{-7}$ mol) instead of PLR (fw 15000~150000).

38-2. 10% 5'-mPEG2k-LMW-chitosan-poly-L-arginine (fw>70000)

A 5'-mPEG2k-LMW-chitosan-poly-L-arginine (fw>70000) conjugate was prepared in the same manner as in Example 37-6, except using PLR (fw>70000, 1.4 mg, $0.2 \times 10^{-7}$ mol) instead of PLR (fw 15000~150000).

Example 39

Preparation of 5'-mPEG2k-LMW-chitosan-poly-L-histidine (fw 5000) Conjugate 39-1. 15% 5'-mPEG2k-LMW-chitosan-poly-L-histidine (fw 5000) conjugate A 5'-mPEG2k-LMW-chitosan-poly-L-histidine (fw 5000) conjugate was prepared in the same manner as in Example 37-5, except using PLH (fw 5000, 0.1 mg, $0.2 \times 10^{-7}$ mol) instead of PLR (fw 15000~150000).

39-2. 10% 5'-mPEG2k-LMW-chitosan-poly-L-histidine (fw 5000) conjugate

A 5'-mPEG2k-LMW-chitosan-poly-L-histidine (fw 5000) conjugate was prepared in the same manner as in Example 37-6, except using PLH (fw 5000, 0.1 mg, $0.2 \times 10^{-7}$ mol) instead of PLR (fw 15000~150000).

Example 40

Preparation of 5'-mPEG2k-LMW-chitosan-poly-L-lysine (fw 9200) Conjugate 40-1. Preparation of 15% 5'-mPEG2k-LMW-chitosan-poly-L-lysine (fw 9200) conjugate A 5'-mPEG2k-LMW-chitosan-poly-L-lysine (fw 9200) conjugate was prepared in the same manner as in Example 37-5, except using PLK (fw 9200, 0.184 mg, $0.2 \times 10^{-7}$ mol) instead of PLR (fw 15000~150000).

40-2. Preparation of 10% 5'-mPEG2k-LMW-chitosan-poly-L-lysine (fw 9200) conjugate A 5'-mPEG2k-LMW-chitosan-poly-L-lysine (fw 9200) conjugate was prepared in the same manner as in Example 37-6, except using PLK (fw 9200, 0.184 mg, $0.2 \times 10^{-7}$ mol) instead of PLR (fw 15000~150000).

Example 41

5'-mPEG2k-MMW-chitosan-poly-L-arginine (fw 15000~70000)

41-1. Preparation of Phth-MMW-chitosan

A Phth-MMW-chitosan was prepared using MMW-chitosan (Aldrich) in the same manner as in Example 37-2.

41-2. Preparation of 15 mol % PEGylated 5'-mPEG2K-MMW-chitosan

A 15 mol % PEGylated 5'-mPEG2K-MMW-chitosan was prepared using phth-MMW-chitosan in the same manner as in Example 37-3.

41-3. Preparation of 10 mol % PEGylated 5'-mPEG2K-MMW-chitosan

A 10 mol % PEGylated 5'-mPEG2K-MMW-chitosan was prepared using phth-MMW-chitosan in the same manner as in Example 37-4.

41-4. 15% 5'-mPEG2k-MMW-chitosan-poly-L-arginine (fw 15000~70000)

A 5'-mPEG2k-MMW-chitosan-poly-L-arginine (fw 15000~70000) conjugate was prepared using 2 mg of 5'-mPEG2K-MMW-chitosan prepared in Example 41-2 in the same manner as in Example 37-5.

41-5. 10% 5'-mPEG2k-MMW-chitosan-poly-L-arginine (fw 15000~70000)

A 5'-mPEG2k-MMW-chitosan-poly-L-arginine (fw 15000~70000) conjugate was prepared using 2 mg of 5'-mPEG2K-MMW-chitosan prepared in Example 41-3 in the same manner as in Example 37-6.

Example 42

Preparation of 5'-mPEG2k-MMW-chitosan-poly-L-arginine (fw>70000) Conjugate 42-1.15% 5'-mPEG2k-MMW-chitosan-poly-L-arginine (fw>70000)

A 5'-mPEG2k-MMW-chitosan-poly-L-arginine (fw>70000) conjugate was prepared using 2 mg of 5'-mPEG2K-MMW-chitosan prepared in Example 41-2 and PLR (fw>70000, 1.4 mg, $0.2 \times 10^{-7}$ mol) in the same manner as in Example 37-5.

42-2. 10% 5'-mPEG2k-MMW-chitosan-poly-L-arginine (fw>70000)

A 5'-mPEG2k-MMW-chitosan-poly-L-arginine (fw>70000) conjugate was prepared using 2 mg of 5'-mPEG2K-MMW-chitosan prepared in Example 41-3 and PLR (fw>70000, 1.4 mg, $0.2 \times 10^{-7}$ mol) in the same manner as in Example 37-6.

Example 43

Preparation of 5'-mPEG2k-MMW-chitosan-poly-L-histidine (fw 5000) Conjugate 43-1. 15% 5'-mPEG2k-MMW-chitosan-poly-L-histidine (fw 5000)

A 5'-mPEG2k-MMW-chitosan-poly-L-histidine (fw 5000) conjugate was prepared using 2 mg of 5'-mPEG2K-MMW-chitosan prepared in Example 41-2 and PLH (fw 5000, 0.1 mg, $0.2 \times 10^{-7}$ mol) in the same manner as in Example 37-5.

43-2. 10% 5'-mPEG2k-MMW-chitosan-poly-L-histidine (fw 5000)

A 5'-mPEG2k-MMW-chitosan-poly-L-histidine (fw 5000) conjugate was prepared using 2 mg of 5'-mPEG2K-MMW-chitosan prepared in Example 41-3 and PLH (fw 5000, 0.1 mg, $0.2 \times 10^{-7}$ mol) in the same manner as in Example 37-6.

Example 44

Preparation of 5'-mPEG2k-MMW-chitosan-poly-L-lysine (fw 9200) Conjugate 44-1. 15% 5'-mPEG2k-MMW-chitosan-poly-L-lysine (fw 9200) conjugate A 5'-mPEG2k-MMW-chitosan-poly-L-lysine (fw 9200) conjugate was prepared using 2 mg of 5'-mPEG2K-MMW-chitosan prepared in Example 41-2 and PLK (fw 9200, 0.184 mg, $0.2 \times 10^{-7}$ mol) in the same manner as in Example 37-5.

44-2. 10% 5'-mPEG2k-MMW-chitosan-poly-L-lysine (fw 9200) conjugate

A 5'-mPEG2k-MMW-chitosan-poly-L-lysine (fw 9200) conjugate was prepared using 2 mg of 5'-mPEG2K-MMW-chitosan prepared in Example 41-3 and PLK (fw 9200, 0.184 mg, $0.2 \times 10^{-7}$ mol) in the same manner as in Example 37-6.

Example 45

Preparation of 5'-mPEG2k-HMW-chitosan-poly-L-arginine (fw 15000~70000) Conjugate 45-1. Preparation of Phth-HMW-chitosan A Phth-HMW-chitosan was prepared using HMW-chitosan (Fluka) in the same manner as in Example 37-2.

45-2. Preparation of 15 mol % PEGylated 5'-mPEG2K-HMW-chitosan

A 15 mol % PEGylated 5'-mPEG2K-HMW-chitosan was prepared using phth-HMW-chitosan in the same manner as in Example 37-3.

45-3. Preparation of 10 mol % PEGylated 5'-mPEG2K-HMW-chitosan

A 10 mol % PEGylated 5'-mPEG2K-HMW-chitosan was prepared using phth-HMW-chitosan in the same manner as in Example 37-4.

45-4. 15% 5'-mPEG2k-HMW-chitosan-poly-L-arginine (fw 15000~70000) conjugate

A 5'-mPEG2k-HMW-chitosan-poly-L-arginine (fw 15000~70000) conjugate was prepared using 2 mg of 5'-mPEG2K-HMW-chitosan prepared in Example 45-2 in the same manner as in Example 37-5.

45-5. 10% 5'-mPEG2k-HMW-chitosan-poly-L-arginine (fw 15000~70000) conjugate

A 5'-mPEG2k-HMW-chitosan-poly-L-arginine (fw 15000~70000) conjugate was prepared using 2 mg of 5'-mPEG2K-HMW-chitosan prepared in Example 45-3 in the same manner as in Example 37-6.

Example 46

Preparation of 5'-mPEG2k-HMW-chitosan-poly-L-arginine (fw>70000) Conjugate 46-1. 15% 5'-mPEG2k-HMW-chitosan-poly-L-arginine (fw>70000)

A 5'-mPEG2k-HMW-chitosan-poly-L-arginine (fw>70000) conjugate was prepared using 2 mg of 5'-mPEG2K-HMW-chitosan prepared in Example 45-2 and PLR (fw>70000, 1.4 mg, $0.2 \times 10^{-7}$ mol) in the same manner as in Example 37-5.

46-2. 10% 5'-mPEG2k-HMW-chitosan-poly-L-arginine (fw>70000)

A 5'-mPEG2k-HMW-chitosan-poly-L-arginine (fw>70000) conjugate was prepared using 2 mg of 5'-mPEG2K-HMW-chitosan prepared in Example 45-3 and PLR (fw>70000, 1.4 mg, $0.2 \times 10^{-7}$ mol) in the same manner as in Example 37-6.

Example 47

Preparation of 5'-mPEG2k-HMW-chitosan-poly-L-histidine (fw 5000) Conjugate 47-1. 15% 5'-mPEG2k-HMW-chitosan-poly-L-histidine (fw 5000) conjugate A 5'-mPEG2k-HMW-chitosan-poly-L-histidine (fw 5000) conjugate was prepared using 2 mg of 5'-mPEG2K-HMW-chitosan prepared in Example 45-2 and PLH (fw 5000, 0.1 mg, $0.2 \times 10^{-7}$ mol) in the same manner as in Example 37-5.

47-2. 10% 5'-mPEG2k-HMW-chitosan-poly-L-histidine (fw 5000) conjugate

A 5'-mPEG2k-HMW-chitosan-poly-L-histidine (fw 5000) conjugate was prepared using 2 mg of 5'-mPEG2K-HMW-chitosan prepared in Example 45-3 and PLH (fw 5000, 0.1 mg, $0.2 \times 10^{-7}$ mol) in the same manner as in Example 37-6.

Example 48

Preparation of 5'-mPEG2k-HMW-chitosan-poly-L-lysine (fw 9200) Conjugate 48-1. Preparation of 15% 5'-mPEG2k-HMW-chitosan-poly-L-lysine (fw 9200) conjugate A 5'-mPEG2k-HMW-chitosan-poly-L-lysine (fw 9200) conjugate was prepared using 2 mg of 5'-mPEG2K-HMW-chitosan prepared in Example 45-2 and PLK (fw 9200, 0.184 mg, $0.2 \times 10^{-7}$ mol) in the same manner as in Example 37-5.

48-2. Preparation of 10% 5'-mPEG2k-HMW-chitosan-poly-L-lysine (fw 9200) Conjugate A 5'-mPEG2k-HMW-chitosan-poly-L-lysine (fw 9200) conjugate was prepared using 2 mg of 5'-mPEG2K-HMW-chitosan prepared in Example 45-3 and PLK (fw 9200, 0.184 mg, $0.2 \times 10^{-7}$ mol) in the same manner as in Example 37-6.

Example 49

5'-mPEG5k-LMW-chitosan-poly-L-arginine (fw 1500~70000)

49-1. Preparation of mPEG5K—COCH(CH$_3$)Cl mPEG5K—COCH(CH$_3$)Cl was prepared using mPEG2K—OH (1.0 g, 0.2 mmol), 4-dimethylaminopyridine (DMAP; 73.3 mg, 0.18 mmol), triethylamine (TEA; 0.056 ml, 0.4 mmol), and 2-chloropropionyl chloride (0.097 ml, 1.0 mmol) in the same manner as in Example 37-1.

49-2. Preparation of 5 mol % PEGylated 5'-mPEG5K-LMW-chitosan 5 mol % PEGylated 5'-mPEG5K-LMW-chitosan was prepared using mPEG5K—COCH(CH$_3$)Cl prepared in Example 49-1 (180 mg, 36.1 µmol) and chitosan prepared in Example 37-2 in the same manner as in Example 37-3.

49-3. Preparation of 10 mol % PEGylated 5'-mPEG5K-LMW-chitosan 10 mol % PEGylated 5'-mPEG5K-LMW-chitosan was prepared using mPEG5K—COCH(CH$_3$)Cl prepared in Example 49-1 (120 mg, 24.0 µmol) and chitosan prepared in Example 37-2 in the same manner as in Example 37-4.

49-4. 15% 5'-mPEG5k-LMW-chitosan-poly-L-arginine (fw 15000~70000)

2 mg of 5'-mPEG5K-LMW-chitosan prepared in Example 49-2 was dissolved in 1 ml of 50 mM MES buffer solution (pH 4.0), and then mixed with PLR (fw 15000~70000, 0.7 mg, $0.2 \times 10^{-7}$ mol), EDAC (fw 191.7, 383.4 ug, $0.2 \times 10^{-5}$ mol), and Sulfo-NHS (fw 217.14, 434.28 ug, $0.2 \times 10^{-5}$ mol), followed by stirring at room temperature for 24 hrs. The mixture was purified using a centrifugal filter (MWCO 30k), and then freeze-dried to give a 5'-mPEG2k-LMW-chitosan-poly-L-arginine (fw 15000~70000) conjugate.

49-5. 10% 5'-mPEG5k-LMW-chitosan-poly-L-arginine (fw 15000~70000)

2 mg of 5'-mPEG5K-LMW-chitosan prepared in Example 49-3 was dissolved in 1 ml of 50 mM MES buffer solution (pH 4.0), and then mixed with PLR (fw 15000~70000, 0.7 mg, $0.2 \times 10^{-7}$ mol), EDAC (fw 191.7, 383.4 ug, $0.2 \times 10^{-5}$ mol), and Sulfo-NHS (fw 217.14, 434.28 ug, $0.2 \times 10^{-5}$ mol), followed by stirring at room temperature for 24 hrs. The mixture was purified using a centrifugal filter (MWCO 30k), and then freeze-dried to give a 5'-mPEG2k-LMW-chitosan-poly-L-arginine (fw 15000~70000) conjugate.

Example 50

Preparation of 5'-mPEG5k-LMW-chitosan-poly-L-arginine (fw>70000) Conjugate 50-1. 15% 5'-mPEG5k-LMW-chitosan-poly-L-arginine (fw>70000)

A 5'-mPEG5k-LMW-chitosan-poly-L-arginine (fw>70000) conjugate was prepared in the same manner as in Example 49-4, except using PLR (fw>70000, 1.4 mg, $0.2 \times 10^{-7}$ mol) instead of PLR (fw 15000~150000).

50-2. 10% 5'-mPEG5k-LMW-chitosan-poly-L-arginine (fw>70000)

A 5'-mPEG5k-LMW-chitosan-poly-L-arginine (fw>70000) conjugate was prepared in the same manner as in Example 49-5, except using PLR (fw>70000, 1.4 mg, $0.2 \times 10^{-7}$ mol) instead of PLR (fw 15000~150000).

Example 51

Preparation of 5'-mPEG5k-LMW-chitosan-poly-L-histidine (fw 5000) Conjugate 51-1. 15% 5'-mPEG5k-LMW-chitosan-poly-L-histidine (fw 5000) conjugate A 5'-mPEG5k-LMW-chitosan-poly-L-histidine (fw 5000) conjugate was prepared in the same manner as in Example 49-4, except using PLH (fw 5000, 0.1 mg, $0.2 \times 10^{-7}$ mol) instead of PLR (fw 15000~150000).

51-2. 10% 5'-mPEG5k-LMW-chitosan-poly-L-histidine (fw 5000) conjugate

A 5'-mPEG5k-LMW-chitosan-poly-L-histidine (fw 5000) conjugate was prepared in the same manner as in Example 49-5, except using PLH (fw 5000, 0.1 mg, $0.2 \times 10^{-7}$ mol) instead of PLR (fw 15000~150000).

Example 52

Preparation of 5'-mPEG5k-LMW-chitosan-poly-L-lysine (fw 9200) Conjugate 52-1. 15% 5'-mPEG5k-LMW-chitosan-poly-L-lysine (fw 9200) conjugate A 5'-mPEG5k-LMW-chitosan-poly-L-lysine (fw 9200) conjugate was prepared in the same manner as in Example 49-4, except using PLK (fw 9200, 0.184 mg, $0.2 \times 10^{-7}$ mol) instead of PLR (fw 15000~150000).

52-2. 10% 5'-mPEG5k-LMW-chitosan-poly-L-lysine (fw 9200) conjugate

A 5'-mPEG5k-LMW-chitosan-poly-L-lysine (fw 9200) conjugate was prepared in the same manner as in Example 49-5, except using PLK (fw 9200, 0.184 mg, $0.2 \times 10^{-7}$ mol) instead of PLR (fw 15000~150000).

Example 53

Preparation of 5'-mPEG5k-MMW-chitosan-poly-L-arginine (fw 1500-70000) Conjugate 53-1. Preparation of 15 mol % PEGylated 5'-mPEG5K-MMW-chitosan 15 mol % PEGylated 5'-mPEG5K-MMW-chitosan was prepared using mPEG5K—COCH(CH$_3$)Cl prepared in Example 49-1 and chitosan prepared in Example 41-1 in the same manner as in Example 49-2.

53-2. Preparation of 10 mol % PEGylated 5'-mPEG5K-MMW-chitosan 10 mol % PEGylated 5'-mPEG5K-MMW-chitosan was prepared using mPEG5K—COCH(CH$_3$)Cl prepared in Example 49-1 and chitosan prepared in Example 41-1 in the same manner as in Example 49-3.

53-3. 15% 5'-mPEG5k-MMW-chitosan-poly-L-arginine (fw 15000~70000)

A 5'-mPEG5k-MMW-chitosan-poly-L-arginine (fw 15000~70000) conjugate was prepared using 2 mg of 5'-mPEG5K-MMW-chitosan prepared in Example 53-1 in the same manner as in Example 49-4.

53-4. 10% 5'-mPEG5k-MMW-chitosan-poly-L-arginine (fw 15000~70000)

A 5'-mPEG5k-MMW-chitosan-poly-L-arginine (fw 15000~70000) conjugate was prepared using 2 mg of 5'-mPEG5K-MMW-chitosan prepared in Example 53-2 in the same manner as in Example 49-5.

Example 54

5'-mPEG5k-MMW-chitosan-poly-L-arginine (fw>70000)

54-1. 15% 5'-mPEG5k-MMW-chitosan-poly-L-arginine (fw>70000)

A 5'-mPEG5k-MMW-chitosan-poly-L-arginine (fw>70000) conjugate was prepared using 2 mg of 5'-mPEG5K-MMW-chitosan prepared in Example 53-1 and PLR (fw>70000, 1.4 mg, $0.2 \times 10^{-7}$ mol) in the same manner as in Example 49-4.

54-2. 10% 5'-mPEG5k-MMW-chitosan-poly-L-arginine (fw>70000)

A 5'-mPEG5k-MMW-chitosan-poly-L-arginine (fw>70000) conjugate was prepared using 2 mg of 5'-mPEG5K-MMW-chitosan prepared in Example 53-2 and PLR (fw>70000, 1.4 mg, $0.2 \times 10^{-7}$ mol) in the same manner as in Example 49-5.

Example 55

Preparation of 5'-mPEG5k-MMW-chitosan-poly-L-histidine (fw 5000) Conjugate 55-1. 15% 5'-mPEG5k-MMW-chitosan-poly-L-histidine (fw 5000)

A 5'-mPEG5k-MMW-chitosan-poly-L-histidine (fw 5000) conjugate was prepared using 2 mg of 5'-mPEG5K-MMW-chitosan prepared in Example 53-1 and PLH (fw 5000, 0.1 mg, $0.2 \times 10^{-7}$ mol) in the same manner as in Example 49-4.

55-2. 10% 5'-mPEG5k-MMW-chitosan-poly-L-histidine (fw 5000)

A 5'-mPEG5k-MMW-chitosan-poly-L-histidine (fw 5000) conjugate was prepared using 2 mg of 5'-mPEG5K-MMW-chitosan prepared in Example 53-2 and PLH (fw 5000, 0.1 mg, $0.2 \times 10^{-7}$ mol) in the same manner as in Example 49-5.

Example 56

Preparation of 5'-mPEG5k-MMW-chitosan-poly-L-lysine (fw 9200) Conjugate 56-1. 15% 5'-mPEG5k-MMW-chitosan-poly-L-lysine (fw 9200) conjugate A 5'-mPEG5k-MMW-chitosan-poly-L-lysine (fw 9200) conjugate was prepared using 2 mg of 5'-mPEG5K-MMW-chitosan prepared in Example 53-1 and PLK (fw 9200, 0.184 mg, $0.2 \times 10^{-7}$ mol) in the same manner as in Example 49-4.

56-2. 10% 5'-mPEG5k-MMW-chitosan-poly-L-lysine (fw 9200) conjugate

A 5'-mPEG5k-MMW-chitosan-poly-L-lysine (fw 9200) conjugate was prepared using 2 mg of 5'-mPEG5K-MMW-chitosan prepared in Example 53-2 and PLK (fw 9200, 0.184 mg, $0.2 \times 10^{-7}$ mol) in the same manner as in Example 49-5.

Example 57

5'-mPEG5k-HMW-chitosan-poly-L-arginine (fw 1500~70000)

57-1. Preparation of 15 mol % PEGylated 5'-mPEG5K-HMW-chitosan 15 mol % PEGylated 5'-mPEG5K-HMW-chitosan was prepared using mPEG5K—COCH(CH$_3$)Cl prepared in Example 49-1 and chitosan prepared in Example 45-1 in the same manner as in Example 49-2.

57-2. Preparation of 10 mol % PEGylated 5'-mPEG5K-HMW-chitosan 10 mol % PEGylated 5'-mPEG5K-HMW-chitosan was prepared using mPEG5K—COCH(CH$_3$)Cl prepared in Example 49-1 and chitosan prepared in Example 45-1 in the same manner as in Example 49-3.

57-3. 15% 5'-mPEG5k-HMW-chitosan-poly-L-arginine (fw 15000~70000) conjugate

A 5'-mPEG5k-HMW-chitosan-poly-L-arginine (fw 15000~70000) conjugate was prepared using 2 mg of 5'-mPEG5K-HMW-chitosan prepared in Example 57-1 in the same manner as in Example 49-4.

57-4. 10% 5'-mPEG5k-HMW-chitosan-poly-L-arginine (fw 15000~70000) conjugate

A 5'-mPEG5k-HMW-chitosan-poly-L-arginine (fw 15000~70000) conjugate was prepared using 2 mg of 5'-mPEG5K-HMW-chitosan prepared in Example 57-2 in the same manner as in Example 49-5.

Example 58

5'-mPEG5k-HMW-chitosan-poly-L-arginine (fw>70000)

58-1. 15% 5'-mPEG5k-HMW-chitosan-poly-L-arginine (fw>70000)

A 5'-mPEG5k-HMW-chitosan-poly-L-arginine (fw>70000) was prepared using 2 mg of 5'-mPEG5K-HMW-chitosan prepared in Example 57-1 and PLR (fw>70000, 1.4 mg, $0.2 \times 10^{-7}$ mol) in the same manner as in Example 49-4.

58-2. 10% 5'-mPEG5k-HMW-chitosan-poly-L-arginine (fw>70000)

A 5'-mPEG5k-HMW-chitosan-poly-L-arginine (fw>70000) was prepared using 2 mg of 5'-mPEG5K-HMW-chitosan prepared in Example 57-2 and PLR (fw>70000, 1.4 mg, $0.2 \times 10^{-7}$ mol) in the same manner as in Example 49-5.

Example 59

Preparation of 5'-mPEG5k-HMW-chitosan-poly-L-histidine (fw 5000) Conjugate 59-1. 15% 5'-mPEG5k-HMW-chitosan-poly-L-histidine (fw 5000) conjugate A 5'-mPEG5k-HMW-chitosan-poly-L-histidine (fw 5000) conjugate was prepared using 2 mg of 5'-mPEG5K-HMW-chitosan prepared in Example 57-1 and PLH (fw 5000, 0.1 mg, $0.2 \times 10^{-7}$ mol) in the same manner as in Example 49-4.

59-2. 10% 5'-mPEG5k-HMW-chitosan-poly-L-histidine (fw 5000) conjugate

A 5'-mPEG5k-HMW-chitosan-poly-L-histidine (fw 5000) conjugate was prepared using 2 mg of 5'-mPEG5K-HMW-chitosan prepared in Example 57-2 and PLH (fw 5000, 0.1 mg, $0.2 \times 10^{-7}$ mol) in the same manner as in Example 49-5.

Example 60

Preparation of
5'-mPEG5k-HMW-chitosan-poly-L-lysine (fw 9200) Conjugate 60-1. 15% 5'-mPEG5k-HMW-chitosan-poly-L-lysine (fw 9200) conjugate A 5'-mPEG5k-HMW-chitosan-poly-L-lysine (fw 9200) conjugate was prepared using 2 mg of 5'-mPEG5K-HMW-chitosan prepared in Example 57-1 and PLK (fw 9200, 0.184 mg, $0.2 \times 10^{-7}$ mol) in the same manner as in Example 49-4.

60-2. 10% 5'-mPEG5k-HMW-chitosan-poly-L-lysine (fw 9200) conjugate

A 5'-mPEG5k-HMW-chitosan-poly-L-lysine (fw 9200) conjugate was prepared using 2 mg of 5'-mPEG5K-HMW-chitosan prepared in Example 57-2 and PLK (fw 9200, 0.184 mg, $0.2 \times 10^{-7}$ mol) in the same manner as in Example 49-5.

Example 61

Preparation of
Man-PEG2k-LMW-chitosan-poly-L-arginine (fw 15000-70000) Conjugate 61-1. Preparation of Man-PEG2K—NHS PEG2K-diamine (0.5 g, 25 µmol) was dissolved in 25 ml of DCM, and Fmoc-OSu (12.6 mg, 37.5 µmol) was added thereto at 0° C., followed by TLC. The stirring was performed to exhaust PEG-diamine. A vacuum distillation apparatus was used to remove DCM. The resultant was dissolved in a small amount of DCM, precipitated in ether, and purified to give Fmoc-PEG-NH$_2$ containing (Fmoc)$_2$-PEG. The PEG-compound, Fmoc-PEG-NH$_2$ was monitored by TLC. The prepared Fmoc-PEG-NH$_2$ (0.46 g, 23 µmol) was dissolved in 23 ml of DCM. Succinic anhydride (23.0 mg, 230 µmol) and pyridine (22.3 µl, 276 µmol) were added thereto, and refluxed under stirring and nitrogen gas at 40-60° C. overnight. The reactant was cooled to room temperature, extracted with DCM, and washed with saturated NH$_4$Cl(aq). Water was removed from the DCM layer with MgSO$_4$, and the vacuum distillation apparatus was used to remove DCM. The resultant was dissolved in a small amount of DCM, precipitated in an excessive amount of ether, and purified to give Fmoc-PEG-COOH containing (Fmoc)$_2$-PEG. The Fmoc-PEG-COOH compound was monitored by TLC, and then dissolved in D$_2$O, followed by 500 MHz $^1$H NMR. The Fmoc-PEG-COOH compound (0.45 g, 22.5 µmol) was dissolved in 50% piperidine/DMF, and stirred for 1.5 hrs for Fmoc deprotection. The reactant was precipitated in an excessive amount of ether, washed with ether, filtered, and purified to give H$_2$N-PEG-COOH containing PEG-diamine. The obtained compound H$_2$N-PEG-COOH (0.4 g, 20 µmol), mannose (10.8 mg, 60 µmol), and imidazole (8.2 mg, 120 µmol) were dissolved in 2 ml of N-methylpyrrolidone (NMP), heated to 60° C., and stirred for 20 hrs. The reactant was cooled to room temperature, extracted with DCM, and washed with saturated NH$_4$Cl(aq). Water was removed from the DCM layer with MgSO$_4$, and the vacuum distillation apparatus was used to remove DCM. The resultant was purified using a silica gel column chromatography. PEG was recovered using DCM/MeOH/NH$_4$OH, and the solvent was removed using the vacuum distillation apparatus. The resultant was dissolved in a small amount of DCM, precipitated in an excessive amount of ether, and purified to give Man-PEG-COOH containing (Man)$_2$-PEG. The Man-PEG-NHS compound was subjected to NMR, so as to confirm the mannose.

A solution of DCC (12.9 mg, 62.5 µmol) in 0.3 ml of DCM was added dropwise to a solution of the Man-PEG-COOH compound (125 mg, 6.25 µmol) and NHS (7.2 mg, 62.5 µmol) dissolved in 1.5 ml of DCM under nitrogen gas below 0° C. for 1 hr. The mixture was stirred for 10-12 hrs while maintaining the low temperature. Filtering was performed to remove the resulting solid (ureas), and precipitated in ether. Recrystallization was performed from EA (ethyl acetate), and purified to give Man-PEG-NHS. The Man-PEG-NHS compound was dissolved in D$_2$O for the confirmation of mannose and dissolved in CDCl$_3$ for the confirmation of NHS, and then subjected to 500 MHz $^1$H NMR.

61-2. 15% Man-PEG2k-LMW-chitosan-poly-L-arginine (fw 15000-70000) conjugate 10 ml of the chitosan solution (fw 50000~150000, 20 mg, $1.24 \times 10^{-4}$ mol of pyranose units) prepared in Example 13-1 and Man-PEG2K—NHS (fw 2000, 37.26 mg, $1.863 \times 10^{-5}$ mol, 15 mol %) prepared in Example 61-1 were mixed, and then subjected to reaction under stirring at room temperature for 24 hrs. The mixture was purified using a centrifugal filter (MWCO 30k) and freeze-dried to give a Man-PEG2K-LMW-chitosan (fw 50000~150000) conjugate (DP 15 mol %). 2 mg of the prepared Man-PEG2K-LMW-chitosan (fw 50000~150000) conjugate were dissolved in 1 ml of 50 mM MES buffer solution (pH 4.0), and then mixed with PLR (fw 15000~70000, 0.7 mg, $0.2 \times 10^{-7}$ mol), EDAC (fw 191.7, 383.4 ug, $0.2 \times 10^{-5}$ mol), Sulfo-NHS (fw 217.14, 434.28 ug, $0.2 \times 10^{-5}$ mol), followed by stirring at room temperature for 24 hrs. The mixture was purified using a centrifugal filter (MWCO 30k) and then freeze-dried to give a Man-PEG2k-LMW-chitosan-poly-L-arginine (fw 15000~70000) conjugate (DP 15 mol %).

Example 62

Preparation of 15% Man-PEG2k -LMW-chitosan-poly-L-arginine (fw>70000) Conjugate

A Man-PEG2k-LMW-chitosan-poly-L-arginine (fw>70000) conjugate (DP 15 mol %) was prepared in the same manner as in Example 61-2, except using PLR (fw>70000, 1.4 mg, $0.2 \times 10^{-7}$ mol) instead of PLR (fw 15000~70000).

Example 63

15% Man-PEG2k-MMW-chitosan-poly-L-arginine (fw 15000~70000)

A Man-PEG2k-MMW-chitosan-poly-L-arginine (fw 15000~70000) conjugate was prepared using 10 ml of chitosan solution (20 mg, $1.24 \times 10^{-4}$ mol of pyranose units) prepared in 17-1 in the same manner as in Example 61-2.

Example 64

Preparation of 15%
Man-PEG2k-MMW-chitosan-poly-L-arginine (fw>70000) Conjugate

A Man-PEG2k-MMW-chitosan-poly-L-arginine (fw>70000) conjugate (DP 15 mol %) was prepared using 10 ml of chitosan solution prepared in Example 17-1 (20 mg, $1.24 \times 10^{-4}$ mol of pyranose units) and PLR (fw>70000, 1.4 mg, $0.2 \times 10^{-7}$ mol) in the same manner as in Example 61-2.

Example 65

Preparation of 15% Man-PEG2k-HMW-chitosan-poly-L-arginine (fw 15000~70000) Conjugate A Man-PEG2k-HMW-chitosan-poly-L-arginine (fw 15000~70000) conjugate (DP 15 mol %) was prepared using 10 ml of chitosan solution prepared in Example 21-1 (20 mg, $1.24 \times 10^{-4}$ mol of pyranose units) in the same manner as in Example 61-2.

Example 66

Preparation of 15% Man-PEG2k-HMW-chitosan-poly-L-arginine (fw>70000) Conjugate

A Man-PEG2k-HMW-chitosan-poly-L-arginine (fw>70000) conjugate was prepared using 10 ml of chitosan solution prepared in Example 21-1 (20 mg, $1.24 \times 10^{-4}$ mol of pyranose units) and PLR (fw>70000, 1.4 mg, $0.2 \times 10^{-7}$ mol) in the same manner as in Example 61-2.

Example 67

Preparation of Complex of Chitosan Based Conjugate and Small Interfering RNA 67-1. Preparation of complex of cationic polymer conjugate and small interfering RNA A sequence of survivin-specific small interfering RNA that inhibits the expression of mouse survivin (derived from *Mus musculus*, NCBI accession number NM_001168) was determined using a siRNA design program, and provided by Samchully Pharmaceutical Co (Seoul, Korea). As a cationic polymer delivery system, chitosan (Sigma, USA), polyarginine (Sigma, USA), and the chitosan-polyarginine conjugates and chitosan-polyarginine-polyethylene glycol conjugates in Comparative Examples 1 and 2 and Examples were prepared in an aqueous solution for further use.

67-2. Confirmation of complex formation of small interfering RNA and cationic polymer In order to prepare a complex of small interfering RNA and cationic polymer, chitosan, polyarginine, and chitosan-polyarginine solution prepared in Comparative Examples 1 and 2, and Example 6-2 or chitosan-polyarginine-polyethylene glycol solution prepared in Example 45-5 were mixed with the survivin-specific small interfering RNA in various ratios, and then left at 37° C. for 30 min, followed by agarose gel electrophoresis.

Figure 6:
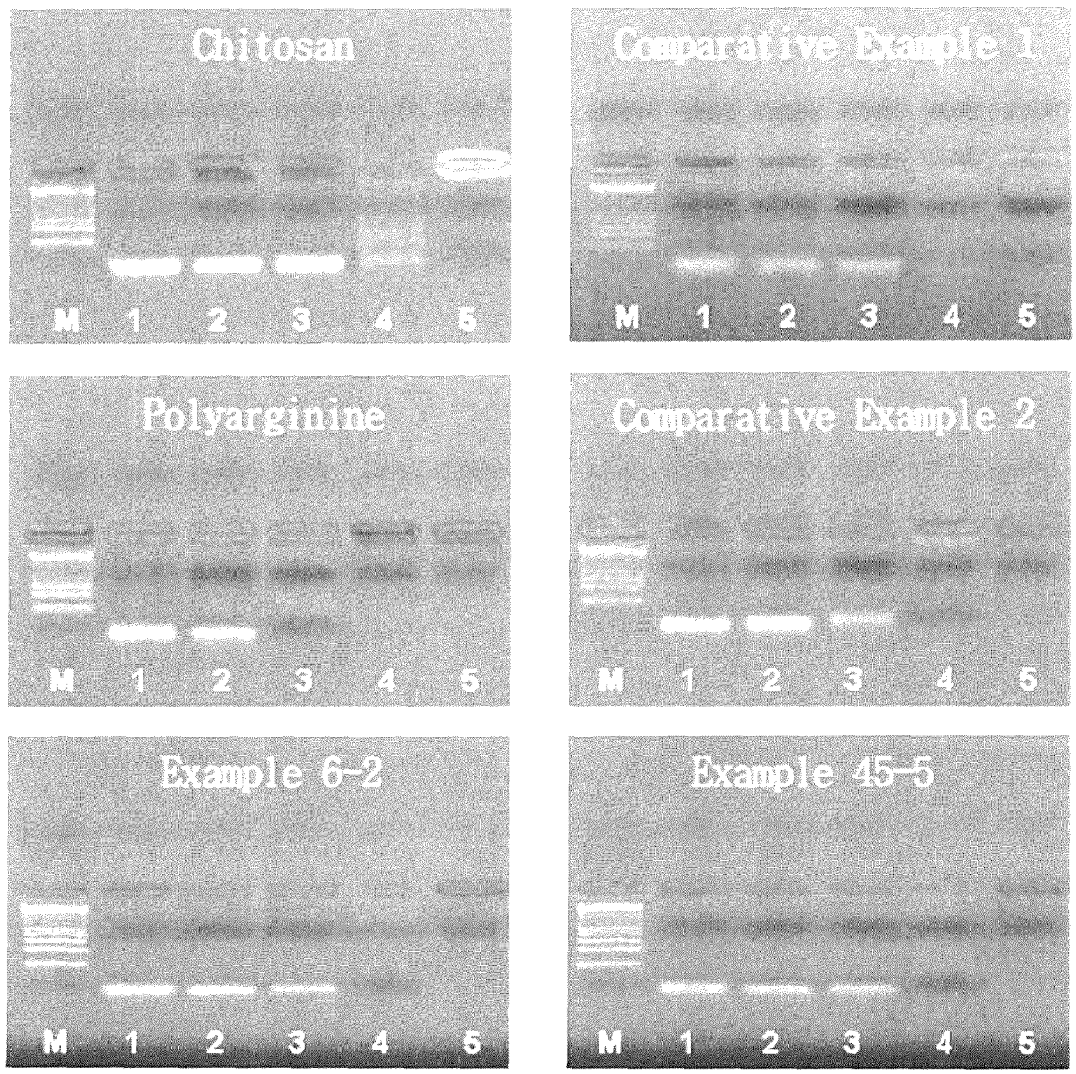
FIG. 6 shows the result of electrophoresis of each complex of chitosan, polyarginine, chitosan-polyarginine and small interfering RNA.

As shown FIG. 6, it was found that as the amount of chitosan-polyarginine (Example 6-2) increased, the amount of small interfering RNA decreased, which indicates that the amount of small interfering RNA that was involved in the complex formation increased due to the complex formation with chitosan-polyarginine. Further, it was found that as the amount of chitosan-polyarginine-polyethylene glycol (Example 45-4) increased, the amount of small interfering RNA decreased, which indicates that the amount of small interfering RNA that was involved in the complex formation increased due to the complex formation with chitosan-polyarginine-polyethylene glycol.

Example 68

Figure 7:
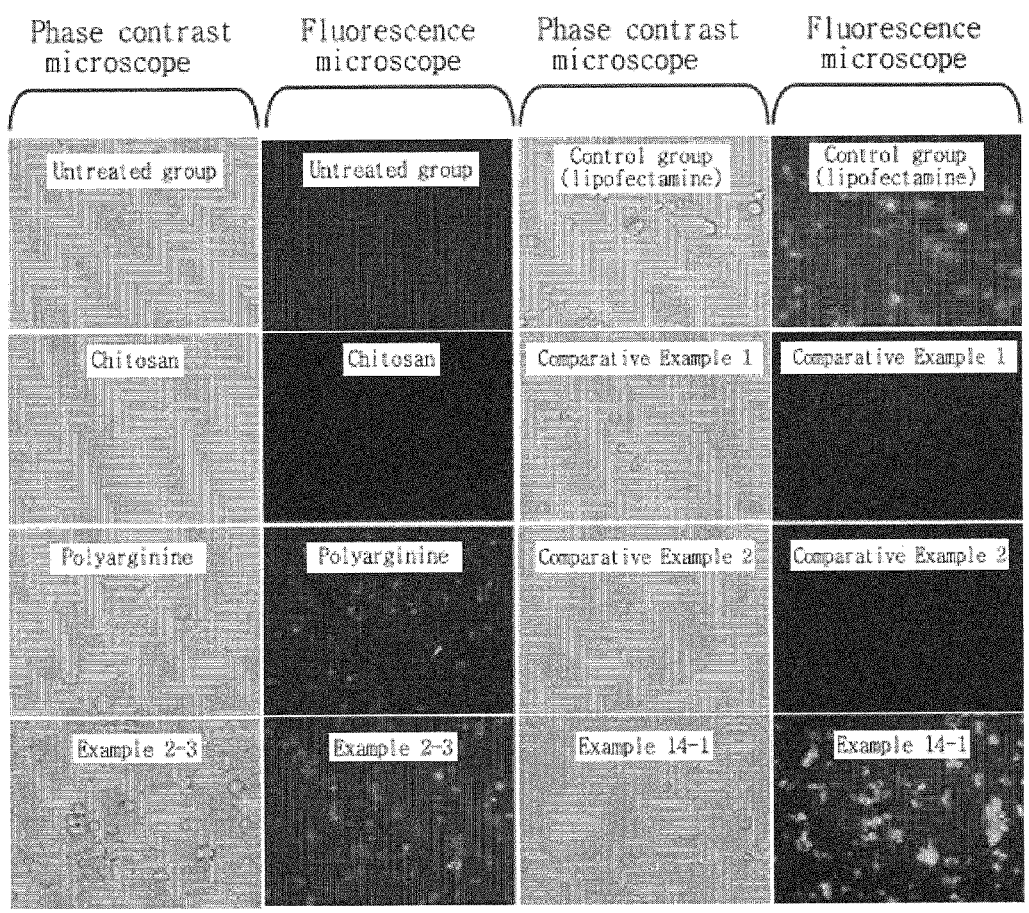
FIG. 7 shows in vivo transfer efficiency of cationic polymer delivery systems into the hepatoma cell line (hepa 1-6), which was compared under a fluorescence microscope using fluorescein labeled RNA.
Figure 8:
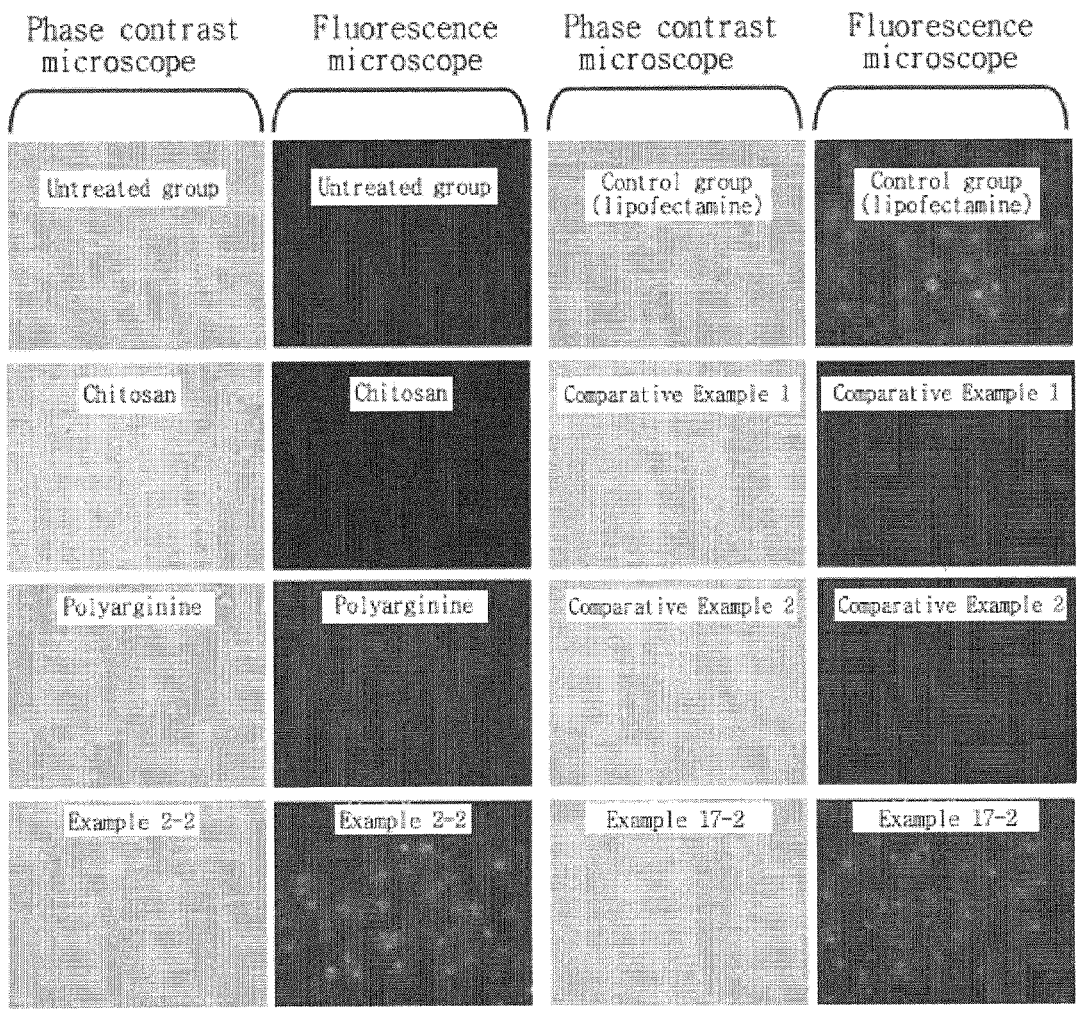
FIG. 8 shows in vivo transfer efficiency of cationic polymer delivery systems into the epithelial cell line (VK2 cell), which was compared under a fluorescence microscope using fluorescein labeled RNA.

Evaluation of In Vivo Transfection Efficiency of Chitosan Polymer Conjugate Using Fluorescein Labeled RNA Fluorescein labeled RNA (Flu-dsRNA, Invitrogen, USA) were mixed with chitosan, the conjugate of chitosan and polyethylene glycol (Comparative Example 1), polyarginine, the double conjugate of polyarginine and polyethylene glycol (Comparative Example 2), the double conjugate of chitosan and polyarginine (Example 2-3), the triple conjugate of chitosan, polyarginine, and polyethylene glycol (Example 14-1), respectively. Then, each mixture was left at 37° C. for 30 min. A hepatoma cell line, Hepa 1-6 (American Tissue Culture Collection, USA) (see FIG. 7) and an epithelial cell line, VK2 (American Tissue Culture Collection, USA) (see FIG. 8) were treated with each mixture. After 24 hrs, the amounts of fluorescein labeled RNA transferred into the cells were observed under a fluorescence microscope. As shown in FIG. 7, in each cell treated with chitosan only and the double conjugate of chitosan and polyethylene glycol (Comparative Example 1) as a delivery system, the lowest transfection efficiency was observed, and in the cell treated with polyarginine only, higher transfection efficiency was observed than that treated with chitosan only. Meanwhile, in the cell treated with the conjugate of chitosan and polyarginine (Example 2-3), the in vivo transfection efficiency was increased. Further, in the cell treated with the triple conjugate of chitosan, polyarginine and polyethylene glycol (Example 14-1), the higher transfection efficiency was observed, as compared to that treated with the double conjugate of polyarginine and polyethylene glycol (Comparative Example 2). The evaluation of in vivo transfection efficiency was performed using other cell lines than those shown in FIG. 7. As shown in FIG. 8, in each cell treated with the conjugates of Examples 2-2 and 17-2, higher transfection efficiency was observed, as compared to each cell treated with chitosan, polyarginine, and the conjugates of Comparative Examples 1 and 2.

Example 69

Evaluation of In Vivo Transfection Efficiency of Chitosan Polymer Conjugate: Inhibition of Target Protein Expression by Transferred Small Interfering RNA From the result of Example 68 using fluorescein labeled RNA, it was found that the chitosan-polyarginine conjugate and the chitosan-polyarginine-polyethylene glycol conjugate exhibited high transfection efficiency. Additionally, to evaluate whether the transferred small interfering RNA has a desired biological function in vivo, the inhibition of target protein expression was evaluated.

The survivin-specific small interfering RNA and the hepatoma cell line, Hepa 1-6 were used. As a delivery system, chitosan, the conjugate of chitosan and polyethylene glycol (Comparative Example 1), polyarginine, the conjugate of polyarginine and polyethylene glycol (Comparative Example 2), the double conjugate of chitosan and polyarginine (Example 5-3), the triple conjugate of chitosan, polyarginine and polyethylene glycol (Example 42-2) were used, respectively.

The hepatoma cell line, Hepa 1-6 was cultured in DMEM (Dulbecco's modified eagles medium) containing 10% bovine serum albumin, and treated with a complex of cationic polymer chitosan conjugate and siRNA, followed by culturing for 24 hrs. Then, the cell was washed, and mRNA was isolated and purified from the cell using a TRIzol™ (Invitrogen, USA). Reverse Transcription Polymerase Chain Reaction (RT-PCR) was performed using survivin specific primers and primers specific to glyceraldehyde 3-phosphate dehydrogenase (GAPDH) that is a comparative gene, so as to quantify the expression level of survivin mRNA expression.

First, 1 ug of the purified RNA was added to a RT-PreMix purchased from Bioneer Co. to prepare a complementary DNA strand (cDNA), and 100 ng of the prepared cDNA was mixed with each 1 ul of 10 pmole sense and antisense primers, 0.1 ul of Taq Polymerase (5 U/ul, Bioneer Co., Korea), dNTPs, and 10× reaction buffer to perform RT-PCR. The product was subjected to 1% agarose gel electrophoresis, and then its gel density was quantified using an image analyzer.

Figure 9:
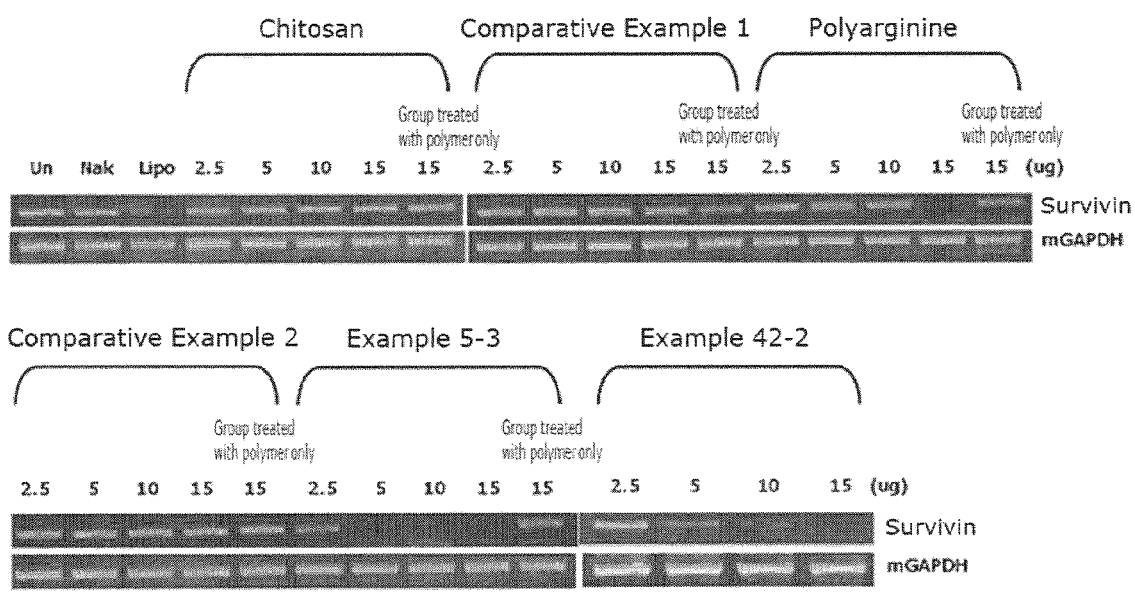
FIG. 9 shows in vivo transfer efficiency of chitosan polymer conjugate, which was evaluated by inhibition of target protein expression by transferred small interfering RNA.

As shown in FIG. 9, in each cell treated with chitosan only, the conjugate of chitosan and polyethylene glycol (Comparative Example 1), and the conjugate of polyarginine and polyethylene glycol (Comparative Example 2), the inhibition of the survivin mRNA expression was not observed. In the cell treated with polyarginine only, the inhibition of the survivin mRNA expression was slightly increased, as compared to that treated with chitosan only. In each cell treated with the conjugate of chitosan and polyarginine (Example 5-3) and the triple conjugate of chitosan, polyarginine and polyethylene glycol, the inhibition of the survivin mRNA expression was significantly increased, as compared to other groups.

Example 70

Cytotoxicity Test in Tumor Cell Line

The following experiment was performed to evaluate cytotoxicity of the complex of small interfering RNA and cationic polymer chitosan derivative. The hepatoma cell line, Hepa 1-6 and the epithelial cell line, VK2 were subjected to a cytotoxicity test with the complex of small interfering RNA and cationic polymer chitosan derivative.

A 3-(4,5-dimethylthiazole-2-yl)-2,5-diphenyl tetrazolium bromide (MTT) reagent was used to perform the cytotoxicity test. 1×10$^5$ cells were seeded in each well, and cultured. Then, the cells were treated with the complex of cationic polymer chitosan derivative (each 15 ug) and siRNA (100 pmole), or siRNA only, respectively. After 24 hrs, the MTT solution was added in a 10% volume of media, and cultured for another 4 hrs. Then, the supernatant was removed, and a 0.04 N hydrochloric isopropanol solution was added thereto. An ELISA reader (Tecan, USA) was used to measure the absorbance at 590 nm. The cell treated with no small interfering RNA was used as a control group. Cell viability was calculated using the following Mathematical Formula.

Cell viability (%)=(OD of experimental group/OD of control group)×100     [Mathematical Formula]

Figure 10:
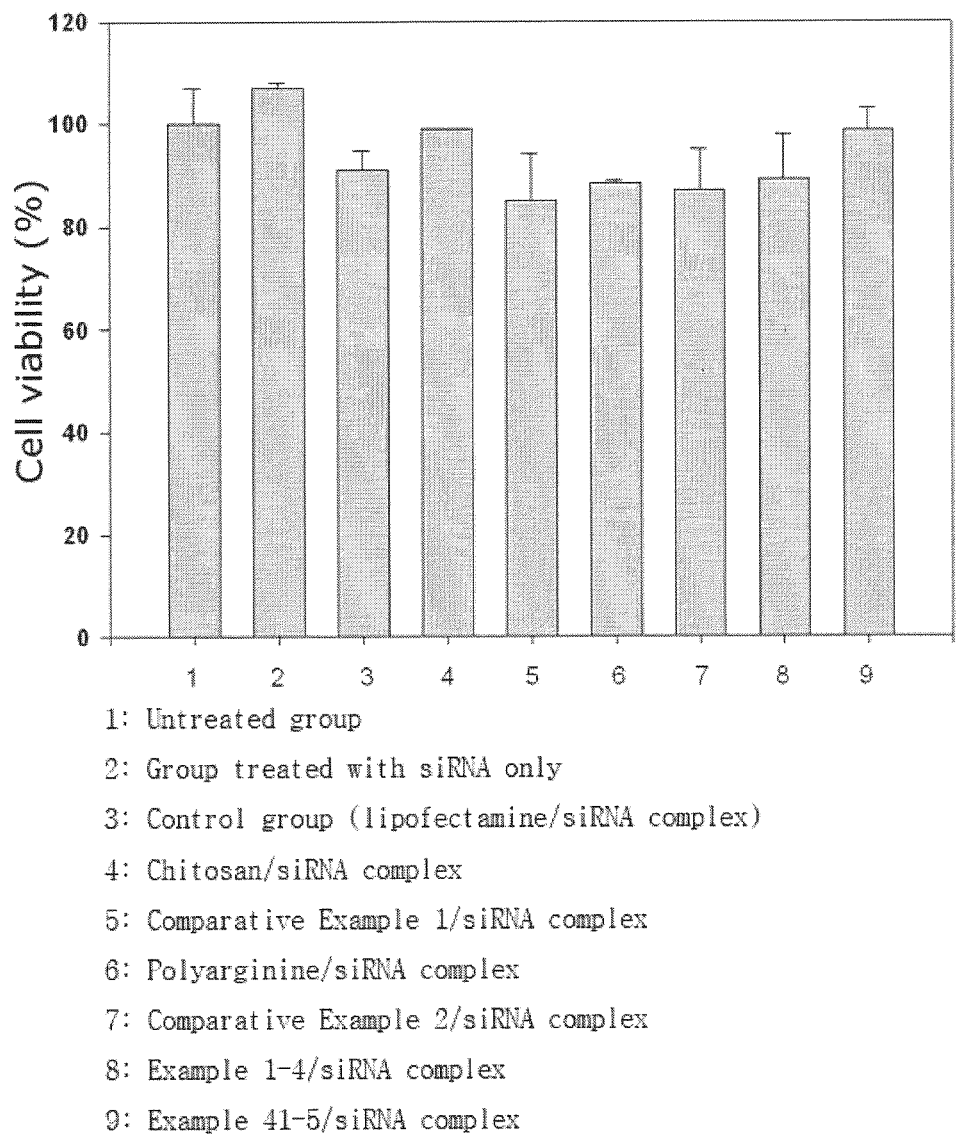
FIG. 10 shows the result of cytotoxicity test on the complex of chitosan polymer conjugate and small interfering RNA in the Hepa 1-6 cell line.
Figure 11:
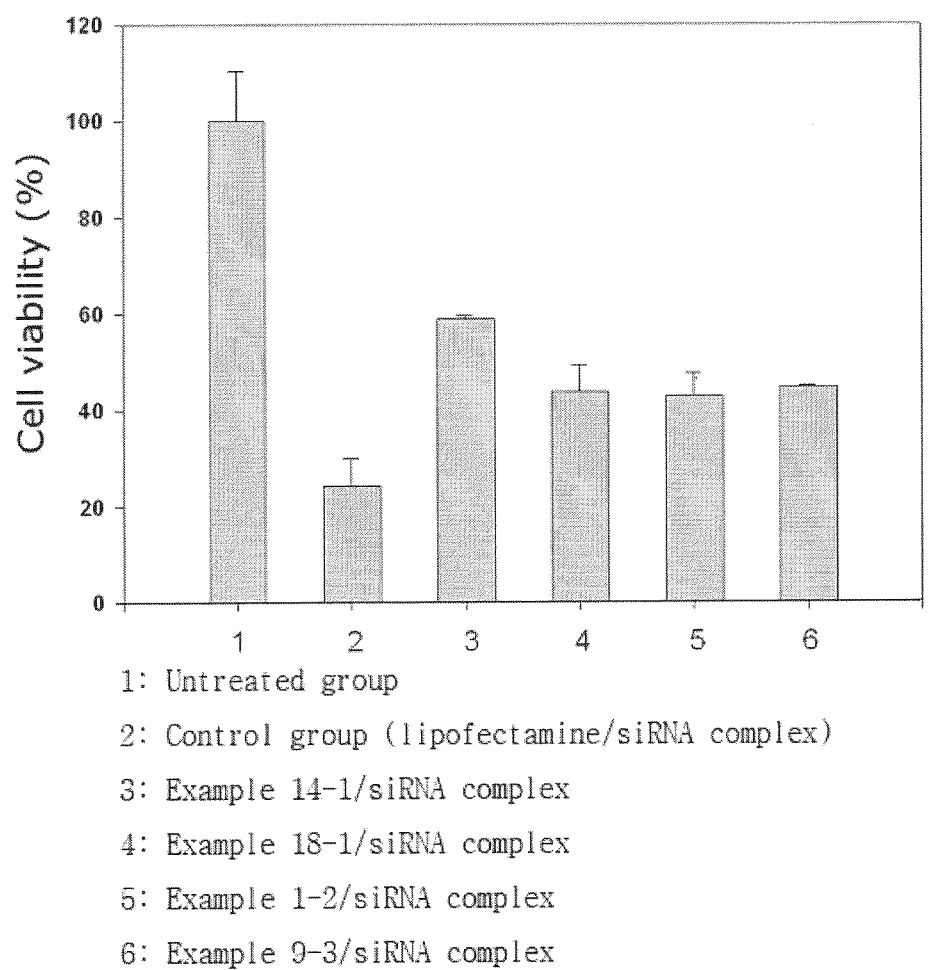
FIG. 11 shows the result of cytotoxicity test on the complex of chitosan polymer conjugate and small interfering RNA in the epithelial cell line (VK2 cell)

As shown in FIG. 10, even though the conjugate of chitosan-polyarginine (Example 1-4) and the conjugate of chitosan-polyethylene glycol (Example 41-5) have increased transfection efficiency, they exhibited low cytotoxicity, as compared to other cationic delivery systems. Further, as shown in FIG. 11, it can be seen that the conjugates of chitosan-polyarginine (Examples 1-2 and 1-3) or the conjugates of chitosan-polyethylene glycol (Examples 14-1 and 18-1) exhibited lower cytotoxicity than a commercially available lipofectamine.

Example 71

Figure 12:
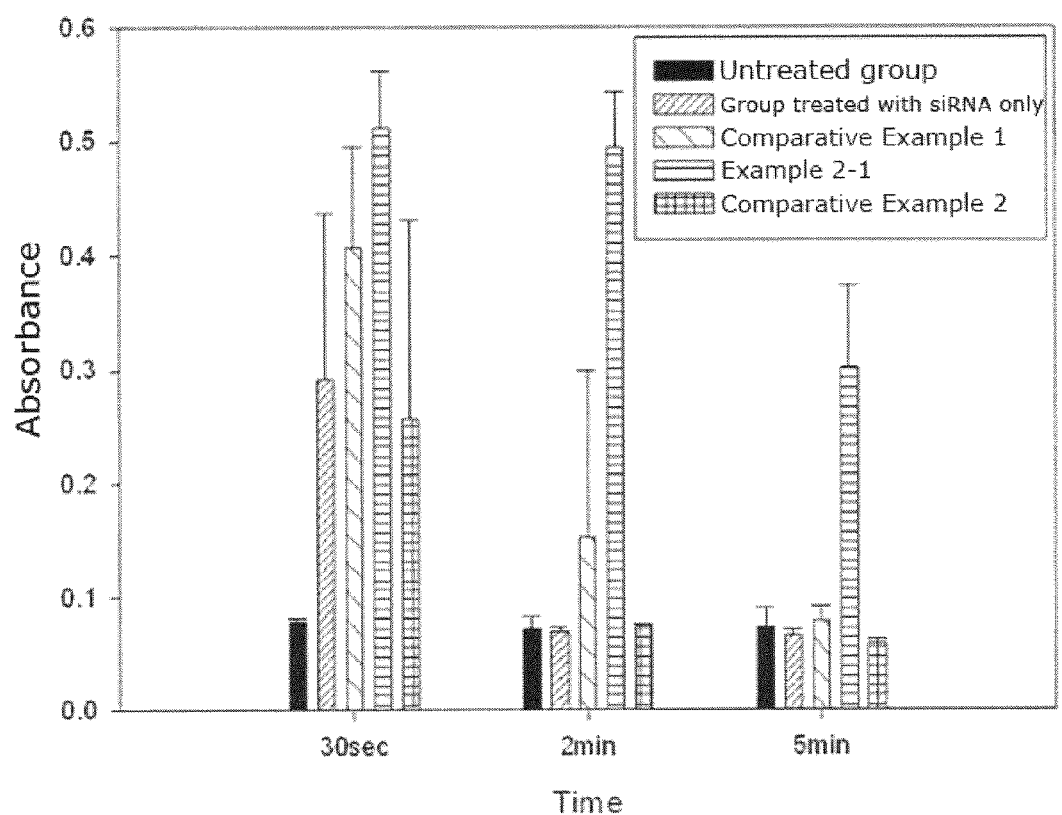
FIG. 12 shows the comparison of the retention of small interfering RNA in blood, which was administered in a complex form with chitosan polymer conjugate and other cationic polymer delivery systems.

Evaluation of Retention of Small Interfering RNA in Blood by Chitosan Polymer Conjugate in Animal Model Each siRNA, in which a double strand is labeled with biotin and dinitrophenol at the phosphate group linked to fifth carbon of its 5' end, and chitosan-polyethylene glycol conjugate (Comparative Example 1), polyarginine-polyethylene glycol conjugate (Comparative Example 2), and chitosan-polyarginine conjugate (Example 2-1) were used for complex formation, respectively. Then, ICR mice were injected via tail vein with each complex. After a predetermined time, blood was collected from the mice, and the amount of siRNA was quantified by immunoassay. Specifically, complex formation was performed using the polymers of Comparative Example 1, Comparative Example 2, and Example 2-1, and small interfering RNA at room temperature for 20 min. As a control group, blood was collected from the group that was not treated with anything and a group that was treated with small interfering RNA only without using any chitosan derivative by an insulin syringe. At the time points of 30 sec, 2 min, and 5 min, blood samples were withdrawn from the tails of mice, and heparin was added thereto. Then, the treated blood samples were added to plates coated with streptavidin, and subjected to reaction at 37° C. for 1 hr. The plates were washed three times, and then a primary antibody (monoclonal mouse anti-DNP IgE; Sigma, Saint Louis, Mo., USA) was diluted (1:5000). The plates were treated with 100 µl of the diluted primary antibody, and left at 37° C. for 1 hr. The plates were washed with a phosphate buffer containing diethyl pyrocarbonate and 0.1% Tween 20 three times. Then, the plates were treated with 100 µl of diluted secondary antibody (goat anti-mouse IgE conjugate HRP; Serotec, Oxford, UK) (1:1000), and left at 37° C. for 1 hr, followed by washing with a phosphate buffer containing diethyl pyrocarbonate and 0.1% tween 20. Then, the plates were color-developed with 100 µl of 3,3',5,5'-tetramethyl benzidine (Turbo TMB™, Pierce, Rockford, USA) solution as a substrate for horseradish peroxidase for 15 min, and the reaction was stopped with 100 µl of 1N $H_2SO_4$. As shown in FIG. 12, in the case of injecting with the complex of small interfering RNA and the chitosan-polyarginine conjugate (Example 2-1), its retention in blood was found to be longer, as compared to each case of injecting with small interfering RNA only, the complex of small interfering RNA and chitosan-polyethylene glycol conjugate (Comparative Example 1), and the complex of small interfering RNA and polyarginine-polyethylene glycol conjugate (Comparative Example 2).

Example 72

Treatment of Liver Fibrosis Using Complex of Polyethylene Glycol-Chitosan-Polyarginine and Target siRNA The small interfering RNA sequence against TGF-β1 gene of *Mus musculus* (mouse origin, NCBI accession number NM_011577) was determined using the siRNA strand known in literatures, and provided by Samchully Pharmaceutical Co. The sequence information for siRNA strand is as follows: 5'-AACUGUAUUCCGUCUCCUUGG-3' and 5'-AACCAAGGAGACGGAAUACAG-3'. The polyethylene glycol-chitosan-polyarginine conjugate in Example 37-6 was made to a 10 mg/ml solution, and siRNA was made to a 1 mg/ml solution.

In order to induce liver fibrosis, CCl$_4$ (Carbon Tetrachloride, 1.5 μl per body weight of individual mouse) and corn oil (4.5 μl per body weight of individual mouse) were mixed in a ratio of 1:3, and administered by intraperitoneal injection. Liver fibrosis was confirmed by collagen staining. 6-week-old female mice (average body weight of 20 grams) were used to perform the experiment for 14 days. During the experimental period, the liver fibrosis-inducing drug was administered by intraperitoneal injection four times. A complex of polyethylene glycol-chitosan-polyarginine conjugate and target siRNA (5 μl of polyethylene glycol-chitosan-polyarginine solution (50 μg of solid polyethylene glycol-chitosan-polyarginine) and 10 μl of siRNA (10 μg of solid siRNA) in PBS solution at 37° C. for 20 min) were prepared, and administered by intravenous injection eight times. Meanwhile, as a control group, only siRNA was administered without using the polyethylene glycol-chitosan-polyarginine conjugate according to the present invention.

Figure 13:
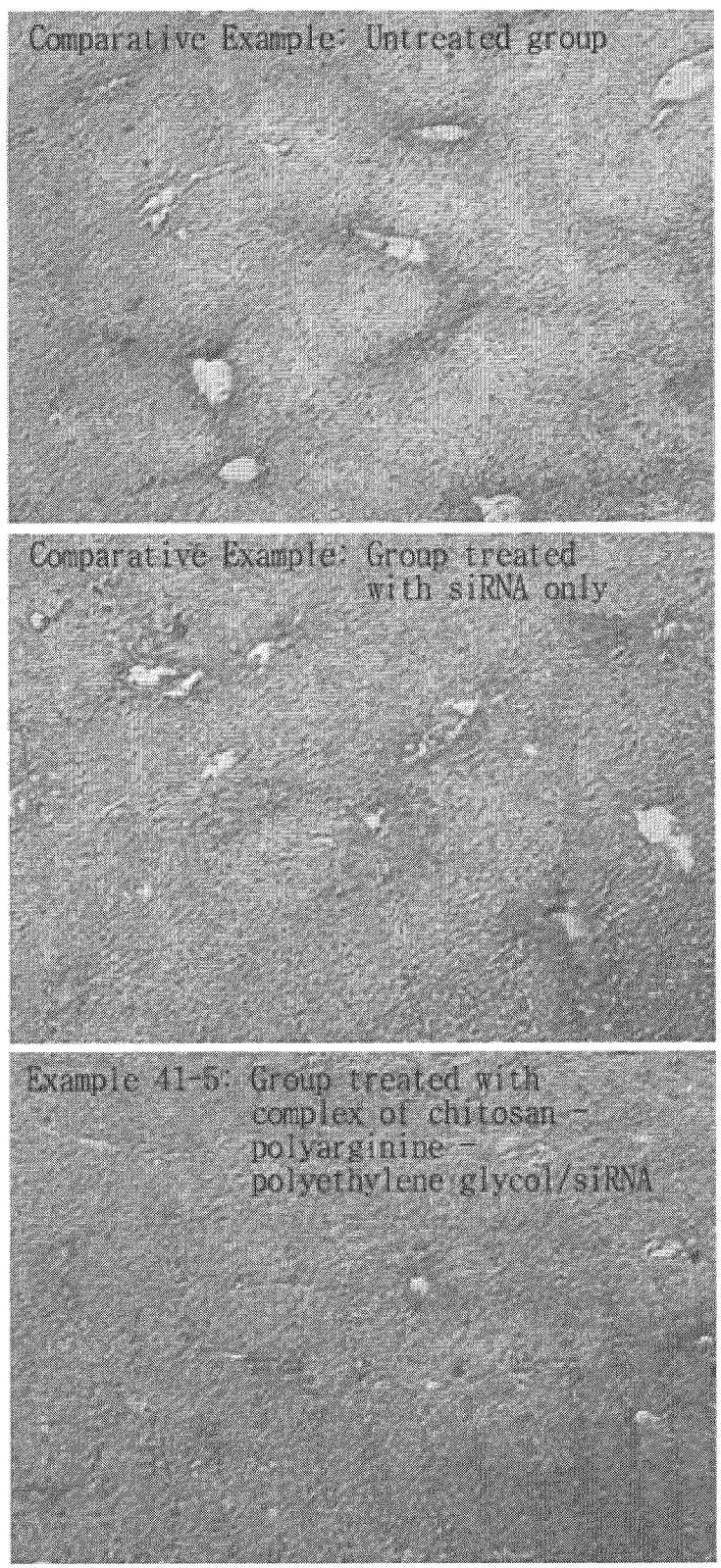
FIG. 13 is a photograph showing the therapeutic effect on liver fibrosis: liver tissue as a negative control (top), liver tissue treated with siRNA only (middle), and liver tissue treated with the complex of siRNA and polyethylene glycol-chitosan-polyarginine conjugate according to the present invention (bottom).

After 14 days, liver samples were taken from the mice, and fixed to prepare paraffin-embedded liver tissues. Cross-sections of liver tissue (5~7 μm) were cut using a microtome, and then collagen staining was performed to assess the degree of liver fibrosis. FIG. 13 is a photograph of liver tissue taken after the above experiment: liver tissue as a negative control (top), liver tissue treated with siRNA only (middle), and liver tissue treated with the complex of siRNA and polyethylene glycol-chitosan-polyarginine conjugate according to the present invention (bottom). From the result, it was found that excellent therapeutic effect can be achieved by using the complex of siRNA and polyethylene glycol-chitosan-polyarginine conjugate according to the present invention, as compared to target siRNA only.

INDUSTRIAL APPLICABILITY

As described above, the chitosan based cationic polymer conjugate of the present invention forms a complex with gene medicine such as small interfering RNA (siRNA) to efficiently transfer the gene material into cells with low cytotoxicity. Accordingly, the conjugate can be used to effectively transfer and express a desired small interfering RNA in various cells. Further, the chitosan based cationic polymer conjugate of the present invention can be used for increasing the retention of gene medicine in blood.

The invention claimed is:

1. A chitosan based cationic polymer conjugate, comprising a polyarginine, polyhistidine or polylysine covalently linked by a carboxyl group to an amine group of chitosan.

2. The chitosan based cationic polymer conjugate according to claim 1, comprising a polyarginine covalently linked by a carboxyl group to an amine group of chitosan.

3. The chitosan based cationic polymer conjugate according to claim 1, comprising a polyhistidine covalently linked by a carboxyl group to an amine group of chitosan.

4. The chitosan based cationic polymer conjugate according to claim 1, comprising a polylysine covalently linked by a carboxyl group to an amine group of chitosan.

5. The chitosan based cationic polymer conjugate according to any one of claims 1 and 2-3, further comprising polyethylene glycol covalently linked to chitosan.

6. The chitosan based cationic polymer conjugate according to claim 5, wherein the polyethylene glycol is linked to an amine or hydroxy group of chitosan.

7. The chitosan based cationic polymer conjugate according to claim 5, wherein the polyethylene glycol is modified with a sugar moiety.

8. A composition for gene delivery into a living body or cell, comprising a gene medicine and the chitosan based cationic polymer conjugate according to claim 5.

9. The composition for gene delivery according to claim 8, wherein the gene medicine is a small interfering RNA or plasmid DNA.

10. The composition for gene delivery according to claim 9, wherein the cell constitutes a mucosal area or mucosal tissue.

11. A gene delivery composition for increasing the retention of gene medicine in blood, comprising a gene medicine and the chitosan based cationic polymer conjugate according to any one of claims 1 and 2-4.

12. The gene delivery composition according to claim 11, wherein the gene medicine is a small interfering RNA or plasmid DNA.

13. A method for preparing the chitosan based cationic polymer conjugate according to claim 1, comprising the step of mixing and stirring chitosan and polyarginine, polyhistidine or polylysine in an aqueous solution in the presence of a coupling agent for carboxyl group.

14. The method for preparing the chitosan based cationic polymer conjugate according to claim 13, wherein a molar ratio of chitosan:polyarginine is 1:1 to 1:10.

15. The method for preparing the chitosan based cationic polymer conjugate according to claim 13, further comprising the step of mixing and stirring an activated polyethylene glycol with chitosan before mixing chitosan with polyarginine, polyhistidine or polylysine, or the step of mixing and stirring chitosan with polyarginine, polyhistidine or polylysine, and then mixing and stirring the produced chitosan-polyarginine, polyhistidine or polylysine conjugate with an activated polyethylene glycol.

16. The method for preparing the chitosan based cationic polymer conjugate according to claim 15, wherein a molar ratio of chitosan:polyethylene glycol is 1:1 to 1:50.

17. The method for preparing the chitosan based cationic polymer conjugate according to claim 15, wherein the activated polyethylene glycol is modified with a sugar moiety.

18. A method for preparing the composition of claim 8, comprising the steps of (1) mixing and stirring chitosan with polyarginine, polyhistidine or polylysine in the presence of a coupling agent for carboxyl group to prepare a chitosan based cationic polymer comprising a polyarginine, polyhistidine or polylysine covalently linked to an amine group of chitosan; and (2) mixing the chitosan based cationic polymer prepared in step (1) with a gene medicine.

19. The method according to claim 18, further comprising the step of mixing and stirring an activated polyethylene glycol with chitosan before mixing chitosan with polyamine or the step of mixing and stirring chitosan with polyarginine, polyhistidine or polylysine, and then mixing and stirring the produced conjugate with an activated polyethylene glycol.

20. The method according to claim 18, wherein the gene medicine is a small interfering RNA or plasmid DNA.

* * * * *

UNITED STATES PATENT AND TRADEMARK OFFICE
CERTIFICATE OF CORRECTION

PATENT NO.         : 8,431,543 B2                                                 Page 1 of 1
APPLICATION NO. : 12/522215
DATED              : April 30, 2013
INVENTOR(S)        : Park et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 643 days.

Signed and Sealed this
Eighth Day of September, 2015

Michelle K. Lee
*Director of the United States Patent and Trademark Office*